United States Patent [19]

Blythin

[11] Patent Number: 4,740,511
[45] Date of Patent: Apr. 26, 1988

[54] METHOD OF TREATING HYPERPROLIFERATIVE SKIN DISEASE

[75] Inventor: David J. Blythin, North Caldwell, N.J.

[73] Assignee: Schering Corporation, Kenilworth, N.J.

[21] Appl. No.: 15,829

[22] Filed: Feb. 18, 1987

[51] Int. Cl.$^4$ .............................................. A61K 31/44
[52] U.S. Cl. .................................... 514/293; 514/290; 514/291; 514/863
[58] Field of Search ................ 514/293, 290, 291, 863

[56] References Cited

U.S. PATENT DOCUMENTS

| | | | |
|---|---|---|---|
| 4,113,731 | 9/1978 | Winters et al. | 546/83 |
| 4,232,017 | 11/1980 | Winters et al. | 546/83 |
| 4,452,800 | 6/1984 | Sherlock | 546/83 |
| 4,680,298 | 7/1987 | Blythin | 514/293 |

Primary Examiner—Leonard Schenkman
Attorney, Agent, or Firm—Richard C. Billups; James R. Nelson; Stephen I. Miller

[57] ABSTRACT

A method of treating hyperproliferative skin disease with substituted quinoline, [1,5]- and [1,8]- naphthyridine and pyrido[2,3-b]pyrazine derivatives is disclosed. The compounds are also anti-allergic, anti-inflammatory and cytoprotective agents. Methods for their preparation and use are disclosed.

30 Claims, No Drawings

METHOD OF TREATING HYPERPROLIFERATIVE SKIN DISEASE

BACKGROUND OF THE INVENTION

The present invention relates to a method of using novel tricyclic compounds which possess anti-allergic, anti-inflammatory, cytoprotective and anti-hyperproliferative skin disease activity. The compounds described herein are the subject of U.S. application Ser. No. 597,887, which was filed Apr. 9, 1984; that Application fails to disclose use of the compounds for the treatment of hyperproliferative skin disease.

The preparation of the compound 2'-methylpyrano-5',6':3,4-(2-oxo-1,2-dihydroquinoline) and its N-phenyl derivative is described in Bull. Soc. Chim. Fr., pp. 364–9 (1968) (C.A. 68:114419c).

SUMMARY OF THE INVENTION

This invention relates to a method of treating hyperproliferative skin disease in a mammal comprising administering to said mammal an anti-hyperproliferative skin disease amount of a compound having the structural formula I

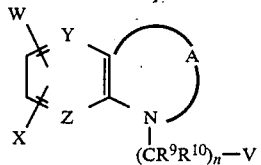

wherein
A is

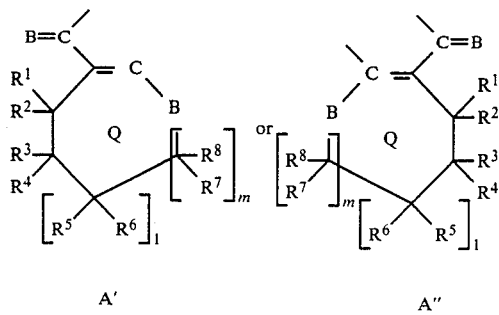

B is independently oxygen or sulfur;
$R^1$–$R^8$ may be the same or different and are hydrogen or alkyl having from 1 to 6 carbon atoms or two adjacent $R^1$–$R^8$ substituents may be combined to form an additional carbon to carbon bond;
l and m may be the same or different and are 0 or 1;
the ring labeled, Q, may optionally contain up to two additional double bonds:
n is 0, 1 or 2:
W and X may be the same or different and are hydrogen, hydroxy, alkyl having from 1 to 6 carbon atoms, halogen, nitro, alkoxy having from 1 to 6 carbon atoms, tri-fluoromethyl, cyano, cycloalkyl having from 3 to 7 carbon atoms, alkenyloxy having from 3 to 6 carbon atoms, alkynyloxy having from 3 to 6 carbon atoms, $S(O)_p$-$R^a$ {wherein p is 0, 1 or 2 and $R^a$ is alkyl having from 1 to 6 carbon atoms}, $NHSO_2R^a$ {wherein $R^a$ is defined herein}, $NHSO_2CF_3$, $NHCOCF_3$, $SP_2NH_2$, $COR_b$ {wherein $R^b$ is OH, $NH_2$ or $OR^a$ (wherein $R^a$ is defined herein)}, O-D-$COR^b$ {wherein D is alkylene having from 1 to 4 carbon atoms and $R^b$ is defined herein}, or $NHCOR^c$ {wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}, or phenoxy {wherein the benzene ring may be substituted with any of the other substituents W and X};
Y and Z may be the same or different and are CH or N;
V is phenyl, naphthyl, indenyl, indanyl, pyridyl, pyrimidinyl, thienyl, furyl or thiazolyl, any of which may be substituted with W and X as defined herein; and
$R^9$ and $R^{10}$ are independently hydrogen or alkyl having from 1 to 6 carbon atoms.

A preferred subgenus of the compounds used in the method of this invention is that wherein B is oxygen.

A more preferred subgenus of compounds is that wherein B is oxygen and Z is nitrogen.

A still more preferred subgenus of compounds is that having the structural formula

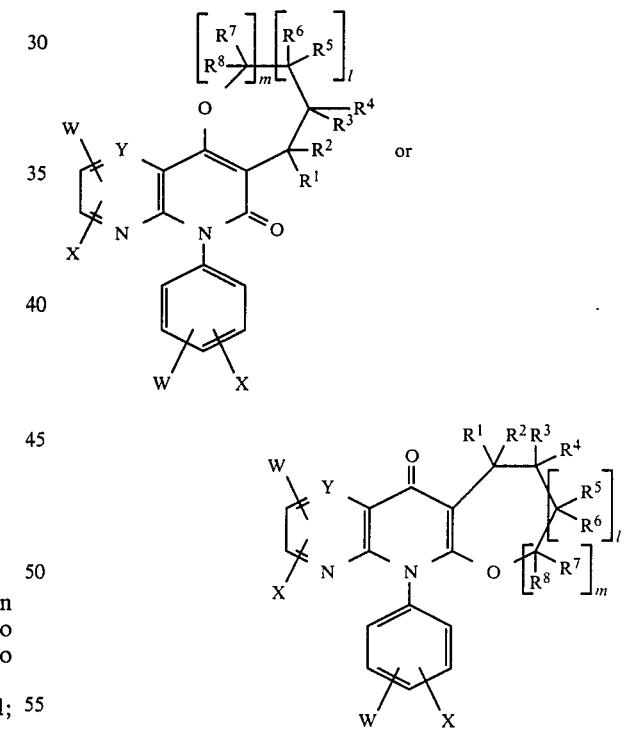

wherein W, X, Y, $R^1$–$R^8$, l and m are as defined herein.

Preferred species used in the method of the invention are those having the names:

3,5-dihydro-5-phenyl-furo[3,2-c][1,8]naphthyridin-4[2H]-one;

6-phenyl-2,3,4,6-tetrahydro-pyrano[3,2-c][1,8]naphthyridin-5-one;

2-methyl-3,5-dihydro-5-phenyl-furo[3,2-c][1,8]naphthyridin-4[2H]-one;

3,9-dihydro-9-phenyl-furo[2,3-b][1,8]naphthyridin-4[2H]-one;

3,9-dihydro-9-(p-methylphenyl)-furo[2,3-b][1,8]naph-thyridin-4[2H]-one;
3,9-dihydro-2-methyl-9-phenyl-furo[2,3-b][1,8]naph-thyridin-4[2H]-one;
3,5-dihydro-5-(p-methylphenyl)-furo[3,2-c][1,8]naph-thyridin-4[2H]-one;
3,5-dihydro-5-(p-fluorophenyl)-furo[3,2-c][1,8]naph-thyridin-4[2H]-one;
3,5-dihydro-5-(m-methoxyphenyl)-furo[3,2-c][1,8]naph-thyridin-4[2H]-one;
3,5-dihydro-5-(m-methylthiophenyl)-furo[3,2-c][1,8]naphthyridin-4[2H]-one;
3,9-dihydro-9-(p-fluorophenyl)-furo[2,3-b][1,8]naph-thyridin-4[2H]-one;
3,9-dihydro-9-(m-methoxyphenyl)-furo[2,3-b][1,8]naph-thyridin-4[2H]-one;
3,9-dihydro-9-(m-methylthiophenyl)-furo[3,2-c][1,8]naphthyridin-4[2H]-one;
3,5-dihydro-5-(3,4-dichlorophenyl)-furo[3,2-c][1,8]naphthyridin-4[2H]-one;
3,5-dihydro-5-(3,4-dichlorophenyl)-2-methyl-furo[3,2-c][1,8]-naphthyridin-4[2H]-one;
3,5-dihydro-5-(4-chlorophenyl)-furo[3,2-c][1,8]naph-thyridin-4[2H]-one;
3,5-dihydro-5-(3-chlorophenyl)-furo[3,2-c][1,8]naph-thyridin-4[2H]-one;
3,5-dihydro-5-(3-chlorophenyl)-2-methyl-furo[3,2-c][1,8]naphthyridin-4[2H]-one;
3,5-dihydro-5-(4-fluorophenyl)-2-methyl-furo[3,2-c][1,8]naphthyridin-4[2H]-one;
3,5-dihydro-5-(3-methoxyphenyl)-2-methyl-furo[3,2-c][1,8]-naphthyridin-4[2H]-one;
3,5-dihydro-5-(3,5-dichlorophenyl)-furo[3,2-c][1,8]naphthyridin-4[2H]-one;
3,5-dihydro-5-(3,5-dichlorophenyl)-2-methyl-furo[3,2-c][1,8]naphthyridin-4[2H]-one;
3,5-dihydro-5-phenyl-2,2-dimethyl-furo[3,2-c][1,8]naphthyridin-4[2H]-one;
3,5-dihydro-5-(3-methylsulfonylaminophenyl)-2-methyl-furo[3,2-c][1,8]-naphthyridin-4[2H]-one;
3,5-dihydro-5-(3-methylsulfonylaminophenyl)-furo[3,2-c][1,8]naphthyridin-4[2H]-one;
3,9-dihydro-9-(3,4-dichlorophenyl)-furo[2,3-b][1,8]naphthyridin-4[2H]-one;
3,9-dihydro-9-(4-chlorophenyl)-furo[2,3-b][1,8]naph-thyridin-4[2H]-one;
3,9-dihydro-9-(3-chlorophenyl)-furo[2,3-b][1,8]naph-thyridin-4[2H]-one;
3,9-dihydro-9-(3-chlorophenyl)-2-methyl-furo[2,3-b][1,8]naphthyridin-4[2H]-one;
3,9-dihydro-9-(4-fluorophenyl)-2-methyl-furo[2,3-b][1,8]naphthyridin-4[2H]-one;
3,9-dihydro-9-(3-methoxyphenyl)-2-methyl-furo[2,3-b][1,8]-naphthyridin-4[2H]-one;
3,9-dihydro-9-(3,5-dichlorophenyl)-furo[2,3-b][1,8]naphthyridin-4[2H]-one;
3,9-dihydro-9-(3,5-dichlorophenyl)-2-methyl-furo[2,3-b][1,8]naphthyridin-4[2H]-one;
3,9-dihydro-9-(3-methylsulfonylaminophenyl)-2-methyl-furo[2,3-b][1,8]-naphthyridin-4[2H]-one;
6-(4-chlorophenyl)-2,3,4,6-tetrahydro-5H-pyrano[3,2-c][1,8]naphthyridin-5-one;
6-(3,4-dichlorophenyl)-2,3,4,6-tetrahydro-5H-pyrano[3,2-c][1,8]naphthyridin-5-one;
6-(4-methoxyphenyl)-2,3,4,6-tetrahydro-5H-pyrano[3,2-c][1,8]naphthyridin-5-one;
6-(4-methylphenyl)-2,3,4,6-tetrahydro-5H-pyrano[3,2-c][1,8]naphthyridin-5-one;
10-(3,4-dichlorophenyl)-2,3,4,10-tetrahydro-5H-pyrano[2,3-b][1,8]naphthyridin-5-one;
10-(4-methoxyphenyl)-2,3,4,10-tetrahydro-5H-pyrano[2,3-b][1,8]naphthyridin-5-one;
10-(4-chlorophenyl)-2,3,4,10-tetrahydro-5H-pyrano[2,3-b][1,8]naphthyridin-5-one;
10-(4-methylphenyl)-2,3,4,10-tetrahydro-5H-pyrano[2,3-b][1,8]naphthyridin-5-one;
10-phenyl-2,3,4,10-tetrahydro-5H-pyrano-[2,3-b][1,8]naphthyridin-5-one;
7-phenyl-3,4,5,7-tetrahydro-oxepino[3,2-c][1,8]naph-thyridin-6[2H]-one;
7-(4-chlorophenyl)-3,4,5,7-tetrahydro-oxepino[3,2-c][1,8]-naphthyridin-6[2H]-one;
7-(3-chlorophenyl)-3,4,5,7-tetrahydro-oxepino[3,2-c][1,8]-naphthyridin-6[2H]-one;
7-(3-methoxyphenyl)-3,4,5,7-tetrahydro-oxepino[3,2-c][1,8]-naphthyridin-6[2H]-one; and
7-(3-hydroxyphenyl)-3,4,5,7-tetrahydro-oxepino[3,2-c][1,8]-naphthyridin-6[2H]-one.

The invention described herein is a method of treating hyperproliferative skin disease in a mammal comprising administering to said mammal an anti-hyperproliferative skin disease effective amounts of a compound of structural formula I.

The invention further encompasses administration of a pharmaceutical composition comprising a compound of structural formula I in combination with a pharmaceutically acceptable carrier.

The invention further encompasses the topical and oral administration of the pharmaceutical composition described above in an amount effective to treat hyperproliferative skin disease in a mammal.

Methods of making the compounds as well as methods of treating allergy, inflammation and ulcers are also disclosed.

DESCRIPTION OF THE INVENTION

The compounds used herein may be prepared from a properly substituted 3-(hydroxyalkyl)-4-hydroxy-1-substituted-[quinolin; 1,5-naphthyridin; or 1,8-naphthyridin]-2(1H)-one, a 7-(hydroxyalkyl)-8-hydroxy-5-substituted-pyrido[2,3-b]pyrazin-6(5H)-one having the structural formula II

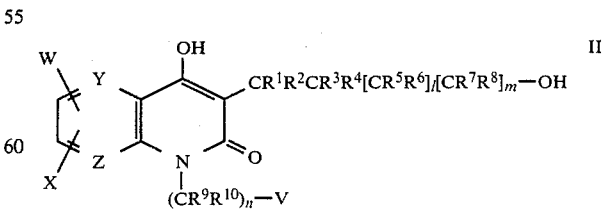

wherein B, V, W, X, Y, Z, $R^1$–$R^{10}$, l, m and n are as defined herein.

Compounds of the invention wherein A is A', and m is 0 i.e., compounds having structural formula I'

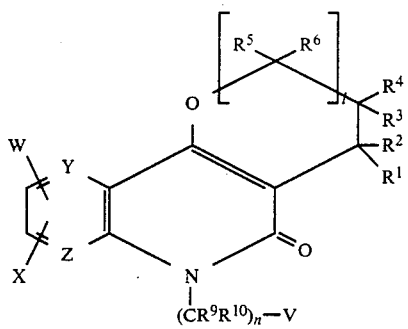

may be prepared by treating a correspondingly substituted compound having structural formula II with a strong aqueous acid solution. Useful acids are sulfuric acid, hydrobromic acid, perchloric acid, trifluoroacetic acid, phosphoric acid and the like. A compatible non-reactive solvent may be utilized to aid solubility, if desired. The use of approximately 30% sulfuric acid without additional solvent is preferred.

In this procedure, the starting compound II is dissolved or suspended in the reaction medium and heated to reflux temperature over a period of about 1 hour. The mixture is maintained at reflux temperature until the reaction is substantially complete. The progress of the reaction may be monitored by standard means, for example thin layer chromatographic means, and is usually substantially completed after about 6 hours. The product may be recovered, for example, by adding the reaction mixture to an excess of cold dilute base solution such as sodium hydroxide, potassium carbonate or the like and isolating the product by standard means such as extraction with an organic solvent or by filtration. Further purification, if desired, may be effected by recrystallization.

The thiated derivatives of I' may be prepared by procedures described below.

Compounds of the invention wherein A is A", i.e., compounds having structural formula I"

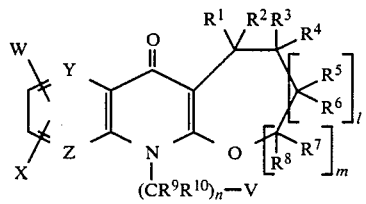

may be prepared by treating a corresponding substituted compound having structural formula II with a dehydrating reagent under anhydrous conditions. Suitable dehydrating reagents for this purpose are phosphorus pentoxide/methanesulfonic acid [known as Eaton's reagent, J. Org. Chem., 35, 4071 (1973)] and thionyl chloride/pyridine/methylene chloride, for example.

In the preferred method for preparing compounds having structural formula I", a correspondingly substituted compound having structural formula II is dissolved or suspended in Eaton's reagent at elevated temperature until the reaction is substantially complete. Temperatures from about 50° to 100° C. are useful. At temperatures of from about 60° to 80° C., the reaction has been observed to be substantially completed in about 1 to about 4 hours.

The progress of the reaction may be monitored by standard means. The product may be recovered, for example, by adding the reaction mixture to an excess of cold dilute base solution such as sodium hydroxide, potassium carbonate or the like and isolating the product by standard means such as extraction with an organic solvent or by filtration. Further purification, if desired, may be effected by recrystallization.

The thiated derivatives of I" may be prepared by procedures described below.

Compounds of the invention wherein A is A' and l and m are both 1, i.e. compounds having the structural formula I'a

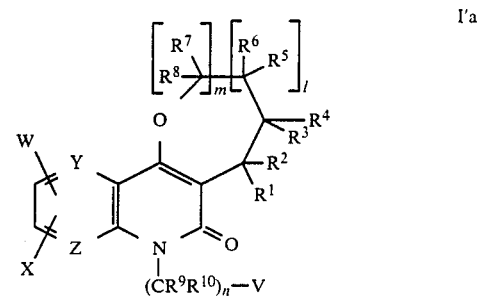

may be prepared by the cyclization of a compound having structural formula IIA

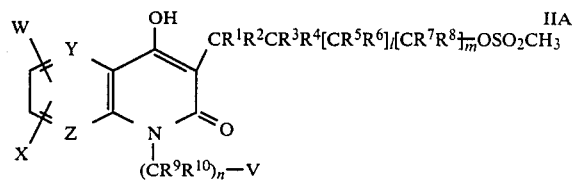

This cyclization is preferably carried out by treating IIA with a base such as cesium carbonate in a convenient solvent such as N,N-dimethylformamide. The product may be isolated and purified by standard methods.

Other base/solvent pairs may be utilized for this cyclization such as sodium or potassium carbonate in N,N-dimethylformamide or N,N-dimethyl acetamide; potassium carbonate in acetone; tetra-n-butylammonium hydroxide, triethylamine or 1,8-diazabicyclo[5.4.0]undec7-ene in methylene chloride or chloroform. In addition, the methanesulfonate leaving group of IIA may be replaced by other leaving groups known in the art such as bromine, chlorine and other sulfonic acid esters derived from acids such as benzenesulfonic acid, p-toluenesulfonic acid and p-bromobenzenesulfonic acid.

The compounds having structural formula II may be prepared by known methods from known starting materials. Exemplary of such starting materials are 2-anilinonicotinic acids prepared, for example, as described in U.S. Pat. No. Re. 26,655, and 2-phenylamino-3-pyrazine carboxylate esters which may be prepared substantially as exemplified herein starting with a 2-amino-3-pyrazine carboxylate ester. 2-Anilino-3-pyrazine carboxylic acid is a known compound, C.A., 75, 20154e (1971), which may be esterified by standard procedures.

The compounds having structural formula IIA may be prepared from the corresponding substituted compound having structural formula II by known methods. For example, compound II may be treated with methanesulfonic acid in the presence of a dehydrating agent such as phosphorus pentoxide (Eaton's reagent).

The compounds having structural formula I' may also be produced from a correspondingly substituted compound having structural formula I''. Thus for example, a compound having structural formula I'' may be treated with a nucleophile such as bromide or iodide anion under anhydrous conditions in a non-reactive solvent such as N,N-dimethylacetamide between about 60° C. and the mixture's reflux temperature for about 2 to about 12 hours to effect this conversion.

Certain compounds of the invention having structural formula I in which one or both of B are sulfur may be prepared from the correspondingly substituted compound having structural formula II by treatment with, for example, Lawesson's Reagent [2,4-bis(4-methoxyphenyl)1,3-dithia-2,4-diphosphetane-2,4-disulfide] in hot toluene. Under these conditions both cyclization of II and thiation are found to occur. Also, reaction of Lawesson's Reagent with compound I' yields mainly a singly thiated product, i.e. the product in which the carbonyl oxygen atom has been replaced by sulfur (a thioamide); whereas —O— is not replaced.

In addition, certain compounds wherein one of the B substituents is oxygen and one is sulfur may be rearranged by treatment with a nucleophile as described above. Thus, for example, a thioamide compound wherein the cyclic B atom is oxygen having structural formula I', may be rearranged to produce a compound having structural formula I'' wherein the cyclic B atom is sulfur and the doubly bonded B atom is oxygen.

The above-described thiation conversions and rearrangements are further described below by use of diagrams. For reasons of convenience and clarity, abbreviated structures are utilized in the diagrams. The references noted on the arrows refer to the procedures of the indicated working examples.

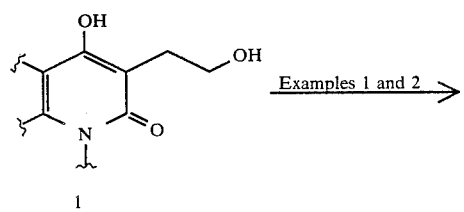

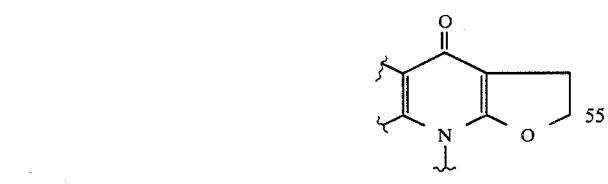

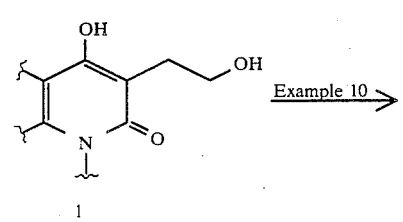

-continued

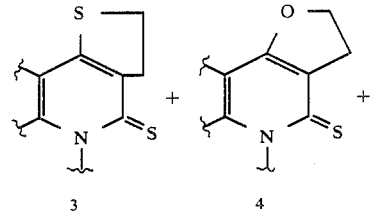

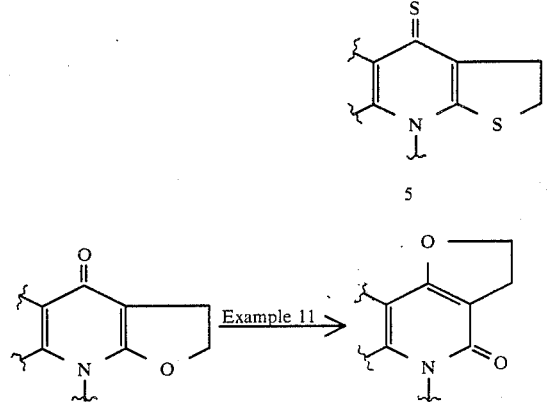

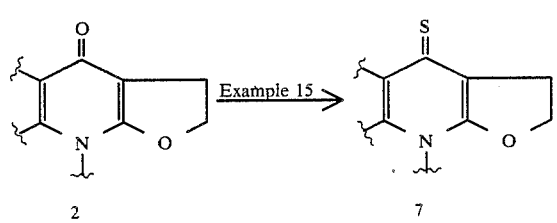

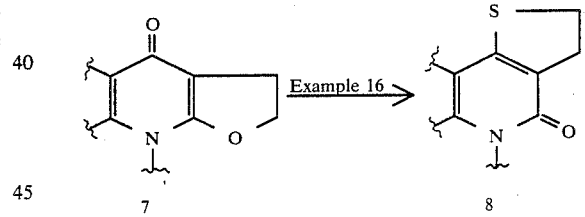

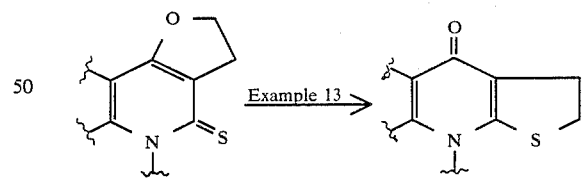

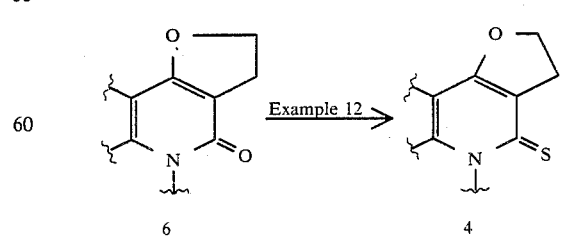

When utilized herein and in the appended claims the below listed terms, unless specified otherwise, are defined as follows:

halogen—fluorine, chlorine, bromine and iodine;

alkyl and alkoxy—comprised of straight and branched carbon chains containing from 1 to 6 carbon atoms;

alkenyloxy—comprised of straight and branched carbon chains containing from 3 to 8 carbon atoms and comprising a carbon to carbon double bond; and alkynyloxy—comprised of straight and branched carbon chains containing from 3 to 8 carbon atoms and comprising a carbon to carbon triple bond.

The compounds used herein may possibly contain two different "B" substituents. It is intended that both may simultaneously be oxygen or sulfur, or that either may be oxygen or sulfur.

In certain compounds, the ring labeled Q, may contain up to two additional double bonds which double bonds are formed by the combination of two adjacent substituents, $R^1$-$R^8$. Thus, for example, when Q is a 7 membered ring (l and m are both equal to 1) it may contain 3 double bonds. When multiple double bonds are present they will be non-cumulative double bonds.

The compounds are comprised of a —$(CR^9R^{10})_n$— substituent wherein the $R^9$ and $R^{10}$ groups may vary independently. Thus, for example, when n equals 2 the following patterns of substitution (wherein hydrogen and $CH_3$ are used to represent any substituent, $R^9$ or $R^{10}$,) are contemplated: —$C(CH_3)_2CH_2$—, —$CH_2C(CH_3)_2$—, —$CH_2CH(CH_3)$—, —$CH(CH_3)CH_2$—, —$(C(CH_3)H)_2$— and the like. In addition when n equals 2, substituents such as —$C(CH_3)_2CH(C_2H_5)$—, —$CH(CH_3)CH(C_2H_5)$—, —$CH(i-C_3H_7)CH(C_2H_5)$— are also contemplated.

Certain compounds used herein may exist in isomeric forms. The invention contemplates all such isomers both in pure form and in admixture, including racemic mixtures.

The compounds of this invention can be used to treat hyperproliferative skin disease in a mammal, and the preferred use disclosed herein is to treat hyperproliferative skin disease. As used herein, hyperproliferative skin disease means any condition a symptom of which is accelerated skin cell production, flaking, scales or papular lesions. Representative examples of hyperproliferative skin disease include psoriasis, eczema, dandruff and the like. Effectiveness of the compounds of formula I for the treatment of hyperproliferative skin disease is demonstrated by the Arachidinic Acid Mouse Ear Test, as described in detail below.

Arachidonic Acid Mouse Ear Test,

Materials and Methods

Charles River, female, CD, (SD) BR mice, 6 weeks old, are caged 8/group and allowed to acclimate 1-3 weeks prior to use.

Arachidonic acid (AA) is dissolved in reagent grade acetone (2 mg/0.01 ml) and stored at $-20°$ C. for a maximum of 1 week prior to use. Inflammatory reactions are induced by applying 0.01 ml of AA to each surface of one ear (4 mg total).

Test drugs are dissolved in either reagent grade acetone or aqueous ethanol (only if insoluble in acetone) at the same doses selected by Opas et al., Fed. Proc. 43, Abstract 2983, p. 1927 (1984) and Young et al., J. Invest. Dermatol. 82, pp. 367-371 (1984). These doses are employed to ensure maximum responses and to overcome any difference in topical absorption which could occur with any drug applied in an aqueous ethanol vehicle.

The test drug is applied 30 minutes prior to challenge with AA.

The severity of the reaction is measured as a function of increased ear weight. A 6 mm punch biopsy is removed 1 hour after AA challenge and weighed to the nearest 0.1 mg. Mean ± standard error and all possible comparisons are made via Duncan's Multiple Range Statistic.

Effectiveness of the compounds used herein is demonstrated using, for example, the compound 3,9-dihydro-9-(3-chlorophenyl)-2-methyl-furo[2,3-b][1,8]naphthyridin-4[2H]-one which exhibits activity at an effective dose ($ED_{50}$) of 0.13 mg which gives 50% inhibition. Based upon the above, the compounds used herein are effective for the treatment of hyperproliferative skin disease. Based upon the test results, the compounds used herein can be administered by any conventional route, e.g., orally, topically, parenterally, etc. in a dosage range of about 0.05 mg/kg to about 50 mg/kg to treat hyperproliferative skin disease.

The compounds used herein may also be used to treat allergy caused diseases, such as allergic chronic obstructive lung diseases. Chronic obstructive lung disease as used herein means disease conditions in which the passage of air into and out of the lungs is obstructed or diminished such as in asthma, bronchitis and the like.

The anti-allergy method of this invention is demonstrated by tests which measure a compound's inhibition of anaphylactic bronchospasm in sensitized guinea pigs having antigen induced bronchoconstriction. For example, the compound 3,5-dihydro-5-phenylfuro[3,2-c][1,8]naphthyridin-4[2H]-one was found to inhibit anaphylactic bronchospasm in such a test procedure when given at an oral dose of 3-5 mg/kg. Said compound was also found to inhibit allergen-induced histamine release from guinea pig and human sensitized tissue. The compounds are therefore effective non-adrenergic, non-anticholinergic antianaphylactic agents. When administered orally they are active at doses ranging from about 0.1 to about 10 mg/kg of body weight; when administered parenterally, e.g., intravenously, the compounds are active at dosages of from about 0.05 to about 5 mg/kg body weight; when administered by inhalation (aerosol or nebulizer) the compounds are active at dosages of from about 0.25 to about 5 mg per puff; one to four puffs may be taken every 4 hours.

The compounds used herein are also useful for the treatment of inflammation. The anti-inflammatory activity of the compounds may be demonstrated by the Reversed Passive Arthus Reaction (RPAR) Synovitis technique as set forth below using male Lewis rats (obtained from Charles River Breeding Laboratories) weighing 200-250 grams. The potency of the compounds is determined using indomethacin as the standard.

RPAR Synovitis Technique

A Lewis rat is dosed orally with drug or placebo one hour prior to intravenous administration of 2.28 mg of bovine serum albumin (BSA) in 0.2 cc of pyrogen-free saline followed by the intraarticular injection of 0.54 mg of rabbit anti-BSA antibody in 0.03 cc of pyrogen-free saline into one knee joint. The contralateral knee is injected with 0.03 cc of pyrogen free saline. All injections are made with the animal under light ether anesthesia. Three hours later the rat is again dosed orally with drug or placebo. All drug doses are split. That is, one-half of the dose is administered before lesion induction and one-half is administered after lesion induction.

The following morning (about 17 hours after lesion induction) the rat is killed and both knee joints are exposed. The subpatellar areolar tissue with attendant synovium is excised and weighed. Differences between the weight of antibody and saline injected knees are considered to represent the inflammatory response for each animal (delta synovial weight). Differences in delta synovial weight between lesion controls and drug-treated rats are evaluated for statistical significance with an analysis of veriance. Relative potencies are determined with a linear regression analysis.

On the basis of the test results, an oral dosage range of from about 5 milligrams per kilogram of body weight per day to about 50 milligrams per kilogram of body weight per day in divided doses taken at about 4 hour intervals is recommended.

The dosage to be administered and the route of administration depends upon the particular compound used, the age and general health of the patient and the severity of the inflammatory condition. Thus, the dose ultimately decided upon must be left to the judgment of a trained health-care practitioner.

The compounds used herein are also useful for the treatment of peptic ulcers. The compounds display chemotherapeutic activity which enables them to relieve the symptoms of peptic ulcer disease, stress ulceration, and promote healing of gastric and/or duodenal ulcers. The antiulcer activity of the compounds is demonstrated by tests which measure the cytoprotective effect in rats. The compounds are also useful as conjunctive therapeutic agents for coadministration with such antiinflammatory/analgesic agents as aspirin, indomethacin, phenylbutazone ibuprofen, naproxen, tolmetin and other agents. The compounds of this invention prevent the untoward side effects of irritation and damage to the gastrointestinal tract caused by such agents.

The compounds of this invention are evaluated for their antiulcer activity characteristics by standard biological testing procedures.

In cytoprotective tests in rats in which ethanol is employed to induce gastrointestinal damage, the compounds of this invention are found to be effective at doses of from about 0.05 to about 50 mg/kg of body weight per day. Preferably the total dosages are administered in 2-4 divided doses per day.

When administered parenterally, e.g. intravenously, the compounds are administered at a dosage range of about 0.01–10 mg/kg of body weight in single or multiple daily doses.

To treat hyperproliferative skin disease, allergy, inflammation or peptic ulcer disease, and prevent and treat drug-induced gastric ulceration, the compounds can be administered in unit dosage forms such as tablets, capsules, pills, powders, granules sterile parenteral solutions or suspensions, suppositories, mechanical delivery devices, e.g. transdermal, and the like.

The compounds of formula I can exist in unsolvated as well as solvated forms, including hydrated forms. In general, the solvated forms, with pharmaceutically acceptable solvents such as water, ethanol and the like are equivalent to the unsolvated forms for purposes of the invention.

For preparing pharmaceutical compositions from the compounds described by this invention, inert, pharmaceutically acceptable carriers can be either solid or liquid. Solid form preparations include powders, tablets dispersible granules, capsules, cachets and suppositories. A solid carrier can be one or more substances which may also act as diluents, flavoring agents, solubilizers, lubricants, suspending agents, binders or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferalby contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets and capsules can be used as solid dosage forms suitable for oral administration.

When used for the treatment of hyperproliferative skin disease, the preferred route of administration is topical. In this preferred method, a pharmaceutical formulation comprising a compound of formula I together with a non-toxic pharmaceutically acceptable topical carrier, usually in concentrations ranging from about 0.001 percent to about 10 percent, preferably from about 0.1 to about 5 percent, is applied several times daily to the affected skin until the condition has improved. Topical applications may then be continued at less frequent intervals (e.g., once a day) to control the condition.

The compounds of formula I may be conveniently applied in a liquid solvent, preferably in a water-miscible liquid carrier made up of hydrophilic liquids having a high solvating action, e.g., a solution which comprises, for example, propylene glycol and polyethylene glycol. Alternatively, the compound may be applied in dry form, such as a powder. Other forms in which the compound may be used topically include creams, lotions, aerosols, dusts and ointments which are prepared by combining the compound with conventional pharmaceutical diluents and carriers commonly used in topical dry, liquid, cream and aerosol formulations.

The ointments and creams may, for example, be formulated with an aqueous oily base with the addition of suitable thickening and/or gelling agents. Such bases may thus, for example, include water and/or oil such as liquid paraffin or vegatable oil, such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulated with an aqueous or oily base and will, in general, also include one or more of the following, namely, stabilizing agents, emulsifying agents, dispensing agents, suspending agents, thickening agents, coloring agents, perfumes and the like.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection. Liquid preparations can also be formulated in solution in aqueous polyethylene glycol solution. Aqueous solutions suitable for oral use can be prepared by adding the active component in water and adding suitable colorants, flavors, stabilizing, sweetening, solubilizing and thickening agents as desired. Aqueous suspensions suitable for oral use can be made, by dispersing the finely divided active component in water with viscous material, i.e., natural or synthetic gums, resins, methylcellulose, sodium carboxymethylcellulose and other well-known suspending agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provides so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules and powders in vials or ampoules. The unit dosage form can also be a capsule, cachet or tablet itself or it can be the appropriate number of any of these in packaged form.

The quantity of active compound in a unit dose of preparation may be varied or adjusted from about 0.1 mg to about 500 mg according to the particular application and the potency of the active ingredient. The compositions can, if desired, also contain other therapeutic agents.

The dosages may be varied depending upon the requirements of the patient, the severity of the condition being treated and the particular compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

EXAMPLE 1

3,9-Dihydro-9-(4-methylphenyl)-furo[2,3-b][1,8]naphthyridin-4(2H)-one

A solution of 4-hydroxy-3-(2-hydroxyethyl)-1-(4-methylphenyl)-1,8-naphthyridin-2(1H)-one (2.2 g.) in Eaton's Reagent (10% P205 in methane sulfonic acid; 40 ml.) was stirred in an atmosphere of nitrogen and heated to 70° C. for 2 hr. After cooling, the product was poured into water, adjusted to pH 4 with NaHCO$_3$, filtered, washed with water, air dried and was recrystallized from isopropanol with decolorization to yield the product, m.p. 246°–248.5° C.

EXAMPLE 2

9-(3,4-Dichlorophenyl)-3,9-dihydro-2-methyl-furo[2,3-b][1,8]naphthyridin-4(2H)-one A solution of 1-(3,4-dichlorophenyl)-4-hydroxy-3-(2-hydroxypropyl)-1,8-naphthyridin-2(1H)-one (5 g.) in Eaton's Reagent (10% P205 in methanesulfonic acid; 100 ml.), under an atmosphere of nitrogen, was heated at 70° C. for 2 hr. The mixture was cooled and poured into water. The pH was adjusted to 7 with NaHCO$_3$. The product was filtered off, washed with water, dried in air, and recrystallized from isopropanol/charcoal to yield the product, m.p. 218°–220.5° C.

The following compounds may be similarly prepared by substituting the appropriate starting material and using the method of Example 1 or 2.

3,9-Dihydro-9-phenyl-furo[2,3-b][1,8]naphthyridin-4(2H)-one, m.p. 245°–247° C.

3,9-Dihydro-2-methyl-9-phenyl-furo[2,3-b][1,8]naphthyridin-4(2H)-one, m.p. 207°–209° C.

3,9-Dihydro-2-(n-butyl)-9-phenyl-furo[2,3-b][1,8]naphthyridin-4(2H)-one, m.p. 169°–170° C.

3,9-Dihydro-9-(4-fluorophenyl)-furo[2,3-b][1,8]naphthyridin-4(2H-)-one, m.p. 244°–246° C.

3,9-Dihydro-2-methyl-9-(4-fluorophenyl)-furo[2,3-b][1,8]naphthyridin-4(2H)-one, m.p. 195°–197.5° C.

3,9-Dihydro-2-(n-butyl)-9-(4-fluorophenyl)furo[2,3-][1,8]naphthyridin-4(2H)-one 3,9-Dihydro-9-(4-chlorophenyl)-furo [2,3-b][1,8]-naphthyridin-4(2H)-one, m.p. 243°–245° C.

3,9-Dihydro-2-methyl-9-(4-chlorophenyl)-furo[2,3-b][1,8]naphthyridin-4(2H)-one 3,9-Dihydro-9-(4-methoxyphenyl)-furo[2,3-b][1,8]naphthyridin-4(2H)-one, m.p. 227°–228° C.

3,9-Dihydro-2-methyl-9-(4-methoxyphenyl)-furo[2,3-b][1,8]naphthyridin-4(2H)-one 3,9-Dihydro-9-(3-methoxyphenyl)-furo[2,3-b][1,8]naphthyridin-4(2H)-one 3,9-Dihydro-2-methyl-9-(3-methoxyphenyl)-furo[2,3-b][1,8]naphthyridin-4(2H)-one, m.p. 194°–196° C.

3,9-Dihydro-9-(3-methylmercaptophenyl)-furo[2,3-b][1,8]naphthyridin-4(2H)-one 3,9-Dihydro-2-methyl-9-(3-methylmercapto-phenyl)-furo[2,3-b][1,8]naphthyridin-4(2H)-one 3,9-Dihydro-9-benzyl-furo[2,3-b][1,8]-naphthyridin-4(2H)-one 3,9-Dihydro-2-methyl-9-benzyl-furo[2,3-b][1,8]-naphthyridin-4(2H)-one 3,9-Dihydro-9-(2-phenylethyl)-furo[2,3-b][1,8]-naphthyridin-4(2H)-one 3,9-Dihydro-2-methyl-9-(2-phenylethyl)-furo[2,3-b][1,8]-naphthyridin-4(2H)-one 3,9-Dihydro-9-(2-thienylmethyl)-furo[2,3-b][1,8]naphthyridin-4(2H)-one
3,9-Dihydro-9-(2-thiazolyl)-furo[2,3-b][1,8]-naphthyridin-4(2H)-one
3,9-Dihydro-9-(2-pyridyl)-furo[2,3-b][1,8]-naphthyridin-4(2H)-one
3,9-Dihydro-9-[2-(2-pyridyl)ethyl]-furo[2,3-b][1,8]naphthyridin-4(2H)-one
3,9-Dihydro-9-(3-chlorophenyl)-furo [2,3-b][1,8]-naphthyridin-4(2H)-one, m.p. >260° C.
3,9-Dihydro-9-(3,5-dichlorophenyl)-furo[2,3-b]1,8]naphthyridin-4(2H)-one, m.p. 279°–281° C. (dec.)
3,9-Dihydro-2-methyl-9-(3,5-dichloroohenyl)furo[2,3-b][1,8]naphthyridin-4(2H)-one, m.p. 230°–233° C.
3,9-Dihydro-9-(2,3-dichlorophenyl)-furo[2,3-b][1,8]naphthyridin-4(2H)-one
3,9-Dihydro-2-methyl-9-(2,3-dichlorophenyl)furo[2,3-b][1,8]naphthyridin-4(2H)-one
3,9-Dihydro-9-(2,5-dichloroohenyl)-furo[2,3-b][1,8]naphthyridin-4(2H)-one
3,9-Dihydro-9-(3-chloro-4-fluorophenvl)-furo[2,3-b][1,8]naphthyridin-4(2H)-one
3,9-Dihydro-2-methyl-9-(3-chloro-4-fluorophenyl)-furo[2,3-b][1,8]naohthyridin-4(2H)-one
3,9-Dihydro-9-(3-trifluoromethylphenyl)-furo[2,3-b][1,8]naphthyridin-4(2H)-one
3,9-Dihydro-2-methyl-9-(3-trifluoromethylphenyl)-furo[2,3-b][1,8]naphthyridin-4(2H)-one
3,9-Dihydro-9-(3,4-dichlorophenyl)-furo[2,3-b][1,8]naphthyridin-4(2H)-one, m.p. >260° C.
3,9-Dihydro-2-methyl-9-(3-methylsulfonylaminophenyl)-furo[2,3-b][1,8]naphthyridin-4(2H)-one, m.p. 260° C.
3,9-Dihydro-9-phenyl-furo[2,3-b]quinolin-4(2H)-one
3,9-Dihydro-2-methyl-9-phenyl-furo[2,3-b]quinolin-4(2H)-one, m.p. 219.5°–221° C.
3,9-Dihydro-2-(n-butyl)-9-phenyl-furo[2,3-b]quinolin-4(2H)-one
3,9-Dihydro-9-(4-fluorophenyl)-furo[2,3-b]quinolin-4(2H)-one
3,9-Dihydro-2-methyl-9-(4-fluorophenyl)-furo[2,3-b]quinolin-4(2H)-one
3,9-Dihydro-2-(n-butyl)-9-(4-fluorophenyl)furo[2,3-b]quinolin-4(2H)-one
3,9-Dihydro-9-(4-chlorophenyl)-furo[2,3-b]quinolin-4(2H)-one
3,9-Dihydro-2-methyl-9-(4-chlorophenyl)-furo[2,3-b]quinolin-4(2H)-one
3,9-Dihydro-9-(3-methoxyphenyl)-furo[2,3-b]quinolin-4(2H)-one
3,9-Dihydro-2-methyl-9-(3-methoxyphenyl)-furo-[2,3-b]quinolin-4(2H)-one
3,9-Dihydro-9-(3-methylmercaptophenyl)-furo[2,3-b]quinolin-4(2H)-one
3,9-Dihydro-2-methyl-9-(3-methylmercaptophenyl)furo[2,3-b]quinolin-4(2H)-one
3,9-Dihydro-9-benzyl-furo[2,3-b]quinolin-4(2H)-one
3,9-Dihydro-2-methyl-9-benzyl-furo[2,3-b]quinolin-4(2H)-one
3,9-Dihydro-9-(2-phenylethyl)-furo[2,3-b]quinolin-4(2H)-one
3,9-Dihydro-2-methyl-9-(2-phenylethyl)-furo-[2,3-b]quinolin-4(2H)-one
3,9-Dihydro-9-(2-thienylmethyl)-furo[2,3-b]quinolin-4(2H)-one
3,9-Dihydro-9-(2-thiazolyl)-furo[2,3-b]quinolin-4(2H)-one
3,9-Dihydro-9-(2-pyridyl)-furo[2,3-b]quinolin4(2H)-one
3,9-Dihydro-9-[2-(2-pyridyl)ethyl]-furo[2,3-b]quinolin-4(2H)-one
3,9-Dihydro-9-(3-chlorophenyl)-furo[2,3-b]quinolin-4(2H)-one
3,9-Dihydro-2-methyl-9-(3-chlorophenyl)-furo[2,3-b]quinolin-4(2H)-one
2,3,4,10-Tetrahydro-10-phenyl-pyrano[2,3-b][1,8]naphthyridin-5-one, m.p. 288°–290° C. (dec.)
2,3,4,10-Tetrahydro-2-methyl-10-phenyl-pyrano[2, 3-b][1,8]naphthyridin-5-one
2,3,4,10-Tetrahydro-10-(4-fluorophenyl)-pyrano2,3-b][1,8]naphthyridin-5-one
2,3,4,10-Tetrahydro-10-(4-chlorophenyl)-pyrano[2,3-b][1,8]naphthyridin-5-one, m.p. 268°–270° C.
2,3,4,10-Tetrahydro-10-(3,4-dichlorophenyl)-pyrano[2,3-b]1,8]naphthyridin-5-one, m.p. >265° C.
2,3,4,10-Tetrahydro-10-(4-methoxylphenyl)-pyrano[2,3-b]1,8]naphthyridin-5-one, m.p. 276°–279° C.
2,3,4,10-Tetrahydro-10-(4-methoxyphenyl)pyrano-[2,3-b}[1,8]naphthyridin-5-one, m.p. 256°–258° C.
2,3,4,10-Tetrahydro-10-(3-methoxyphenyl)pyrano-[2,3-b][1,8]naphthyridin-5-one
2,3,4,10-Tetrahydro-10-(3-methylmercaptophenyl)-pyrano[2,3-b][1,8]naphthyridin-5-one
2,3,4,10-Tetrahydro-10-benzyl-pyrano[2,3-b][1,8]naphthyridin-5-one
2,3,4,10-Tetrahydro-10-(2-phenylethyl)-pyrano[2,3-b]1,8]naphthyridin-5-one
2,3,4,10-Tetrahydro-10-(2-thienylmethyl)pyrano-[2,3-b][1,8]naphthyridin-5-one
2,3,4,10-Tetrahydro-10-(2-thiazolyl)-pyrano[2,3-b][1,8]naphthyridin-5-one
2,3,4,10-Tetrahydro-10-[2-(2-pyridyl)ethyl]pyrano[2,3-b][1,8]naphthyridin-5-one
2,3,4,10-Tetrahydro-10-(3-chlorophenyl)-pyrano[2,3-b][1,8]naphthyridin-5-one
2,3,4,10-Tetrahydro-10-phenyl-pyrano[2,3-b]quinoline-5-one
2,3,4,10-Tetrahydro-2-methyl-10-phenyl-pyrano[2,3-b]quinoline-5-one
2,3,4,10-Tetrahydro-8-chloro-10-phenyl-pyrano[2,3-b]quinoline-5-one
2,3,4,10-Tetrahydro-8-fluoro-10-phenyl-pyrano[2,3-b]quinoline-5-one
2,3,4,10-Tetrahydro-8-methoxy-10-phenyl-pyrano[2,3-b]quinoline-5-one
2,3,4,10-Tetrahydro-8-methyl-10-phenyl-pyrano[2,3-b]quinoline-5-one
2,3,4,10-Tetrahydro-7-chloro-10-phenyl-pyrano[2,3-b]quinoline-5-one
2,3,4,10-Tetrahydro-7-fluoro-10-phenyl-pyrano[2,3-b]quinoline-5-one
2,3,4,10-Tetrahydro-7-methoxy-10-phenyl-pyrano[2,3-b]quinoline-5-one
2,3,4,10-Tetrahydro-10-(4-fluorophenyl)-pyrano[2,3-b]quinoline-5-one
2,3,4,10-Tetrahydro-10-(4-chlorophenyl)-pyrano[2,3-b]quinoline-5-one
2,3,4,10-Tetrahydro-10-(4-methoxyphenyl)pyrano-[2,3-b]quinoline-5-one
2,3,4,10-Tetrahydro-10-(3-methoxyphenyl)pyrano-[2,3-b]quinoline-5-one
2,3,4,10-Tetrahydro-10-(3-methylmercaptophenyl)-pyrano[2,3-b]quinoline-5-one
2,3,4,10-Tetrahydro-10-benzyl-pyrano[2,3-b]quinoline-5-one 2,3,4,10-Tetrahydro-10-(2-phenylethyl)-pyrano[2,3-b]quinoline-5-one
2,3,4,10-Tetrahydro-10-(2-thienylmethyl)pyrano-[2,3-b]quinoline-5-one
2,3,4,10-Tetrahydro-10-(2-thiazolyl)-pyrano-[2,3-b]quinoline-5-one
2,3,4,10-Tetrahydro-10-[2-(2-pyridyl)ethyl]pyrano[2,3-b]quinoline-5-one
2,3,4,10-Tetrahydro-10-(3-chlorophenyl)-pyrano[2,3-b]quinoline-5-one
3,9-Dihydro-9-phenyl-furo[2,3-b][1,5]naphthyridin-4-(2H)-one
3,9-Dihydro-2-methyl-9-phenyl-furo[2,3-b][1,5]naphthyridin-4-(2H)-one
3,9-Dihydro-2-(n-butyl)-9-phenyl-furo[2,3-b][1,5]naphthyridin-4-(2H)-one
3,9-Dihydro-9-(4-fluorophenyl)-furo[2,3-b ][1,5]-naphthyridin-4-(2H)-one
3,9-Dihydro-2-methyl-9-(4-fluorophenyl)-furo[2,3-b][1,5]naphthyridin-4-(2H)-one
3,9-Dihydro-9-(4-chlorophenyl)--furo[2,3-b][1,5]naphthyridin-4-(2H)-one
3,9-Dihydro-9-(4-methoxyphenyl)-furo[2,3-b][1,5]naphthyridin-4-(2H)-one
3,9-Dihydro-9-(4-methylphenyl)-furo[2,3-b][1,5]-naphthyridin-4-(2H)-one
3,9-Dihydro-9-(3,4-dichlorophenyl)-furo[2,3-b][1,5]naphthyridin-4-(2H)-one
3,9-Dihydro-9-(3-methoxyphenyl)-furo[2,3-b][1,5]naphthyridin-4-(2H)-one
3,9-Dihydro-9-(3-methylmercaptophenyl)-furo[2,3-b][1,5]naphthyridin-4-(2H)-one
3,9-Dihydro-9-(3-chlorophenyl)-furo[2,3-b][1,5]-naphthyridin-4-(2H)-one
3,9-Dihydro-9-benzyl-furo[2,3-b][1,5]naphthyridin-4-(2H)-one
3,9-Dihydro-9-(2-thienylmethyl)-furo[2,3-b][1,5]naphthyridin-4-(2H)-one
3,9-Dihydro-9-(2-thiazolyl)-furo[2,3-b][1,5]naphthyridin-4-(2H)-one
2,3,4,10-Tetrahydro-10-phenyl-pyrano[2,3-b][1,5]naphthyridin-5-one
2,3,4,10-Tetrahydro-2-methyl-10-phenyl-pyrano[2,3-b][1,5]naphthyridin-5-one
2,3,4,10-Tetrahydro-10-(4-fluorophenyl)-pyrano[1,5-]naphthyridin-5-one
2,3,4,10-Tetrahydro-10-(4-chlorophenyl)-pyrano[2,3-b][1,5]naphthyridin-5-one
2,3,4,10-Tetrahydro-10-(3-methoxyphenyl)pyrano-[2,3-b][1,5]naphthyridin-5-one
2,3,4,10-Tetrahydro-10-(3-methylmercaptophenyl)-pyrano[2,3-b][1,5]naphthyridin-5-one
2,3,4,10-Tetrahydro-10-(3-chlorophenyl)-pyrano[2,3-b][1,5]naphthyridin-5-one
2,3,4,10-Tetrahydro-10-benzyl-pyrano[2,3-b][1,5]naphthyridin-5-one
2,3,4,10-Tetrahydro-10-(2-thienylmethyl)pyrano-[2,3-b][1,5]naphthyridin-5-one
7,8-Dihydro-5-phenyl-furo[3',2':5,6]pyrido[2,3-b]pyrazin-9(5H)-one
7,8-Dihydro-2-methyl-5-phenyl-furo[3',2':5,6]pyrido[2,3-b]pyrazin-9(5H)-one
7,8-Dihydro-2-(n-butyl)-5-phenyl-furo[3',2':5,6] pyrido[2,3-b]pyrazin-9(5H)-one
7,8-Dihydro-2,3-dimethyl-5-phenyl-furo[3',2':5,6] pyrido[2,3-b]pyrazin-9(5H)-one
7,8-Dihydro-2,3,7-trimethyl-5-phenyl-furo[3',2':5,6-]pyrido[2,3-b]pyrazin-9(5H)-one
7,8-Dihydro-5-(4-fluorophenyl)-furo[3',2':5,6-]pyrido[2,3-b]pyrazin-9(5H)-one
7,8-Dihydro-2-methyl-5-(4-fluorophenyl)-furo[3',2':5,6-]pyrido[2,3-b]pyrazin-9(5H)-one
7,8-Dihydro-2,3-dimethyl-5-(4-fluorophenyl)-furo[3',2':5,6]pyrido[2,3-b]pyrazin-9(5H)-one
7,8-Dihydro-2,3,7-trimethyl-5-(4-fluorophenyl)-furo[3',2':5,6]pyrido[2,3-b]pyrazin-9(5H)-one
7,8-Dihydro-5-(4-chlorophenyl)-furo[3',2':5,6-]pyrido[2,3-b]pyrazin-9(5H)-one
7,8-Dihydro-5-(4-methylphenyl)-furo[3',2':5,6-]pyrido[2,3-b]pyrazin-9(5H)-one
7,8-Dihydro-5-(4-methoxyphenyl)furo[3',2':5,6]-pyrido[2,3-b]pyrazin-9(5H)-one
7,8-Dihydro-5-(3-methoxyphenyl)furo[3',2':5,6]-pyrido[2,3-b]pyrazin-9(5H)-one
7,8-Dihydro-5-(3-methylmercaptophenyl)-furo[3',2':5,6]pyrido[2,3-h]pyrazin-9(5H)-one
7,8-Dihydro-5-(3-chlorophenyl)-furo[3',2':5,6-]pyrido[2,3-b]pyrazin-9(5H)-one
5,7,8,9-Tetrahydro-5-phenyl-10H-pyrano[3',2':5,6-]pyrido[2,3-b]pyrazin-10-one
5,7,8,9-Tetrahydro-7-methyl-5-phenyl-10H-pyrano-[3',2':5,6]pyrido[2,3-b]pyrazin-10-one
5,7,8,9-Tetrahydro-5-(4-fluorophenyl)-10H-pyrano[3',2':5,6]pyrido[2,3-b]pyrazin-10-one
5,7,8,9-Tetrahydro-2,3-dimethyl-5-(4-fluorophenyl)-10H-pyrano[3',2':5,6]pyrido[2,3-b]pyrazin10-one
5,7,8,9-Tetrahydro-7-methyl-5-(4-fluorophenyl)-10H-pyrano[3',2':5,6]pyrido[2,3-b]pyrazin-10-one
5,7,8,9-Tetrahydro-5-(3-methoxyphenyl)-10H-pyrano[3',2':5,6]pyrido[2,3-b]pyrazin-10-one
5,7,8,9-Tetrahydro-5-(3-methylmercaptophenyl)10H-pyrano[3',2':5,6]pyrido[2,3-b]pyrazin-10-one
5,7,8,9-Tetrahydro-5-(3-chlorophenyl)-10H-pyrano[3',2':5,6]pyrido[2,3-b]pyrazin-10-one
5,7,8,9-Tetrahydro-7-methyl-5-(3-methoxyphenyl)-10H-pyrano[3',2':5,6]pyrido[2,3-b]pyrazin10-one
5,7,8,9-Tetrahydro-7-methyl-5-(3-chlorophenyl)10H-pyrano[3',2':5,6]pyrido[2,3-b]pyrazin-10-one

EXAMPLE 3

3,9-Dihydro-2-methyl-9-phenyl-furo[2,3-b][1,8]naphthyridin-4(2H)-one

A suspension of 4-hydroxy-3-(2-hydroxypropyl)1-phenyl-1,8-naphthyridin-2(1H)-one (1 g.) in CH2CL2 was stirred in an atmosphere of nitrogen. To this was added pyridine (1.5 ml.). To this mixture was added a solution of $SOCl_2$ (1.5 ml.) in $CH_2Cl_2$ (10 ml.) dropwise over a period of 15 minutes. The mixture was stirred overnight at room temperature then water was added. The $CH_2Cl_2$ layer was separated, dried and evaporated. Recrystallization from isopropanol yielded the product, m.p. 207°–209° C.

EXAMPLE 4

5-(3,4-Dichlorophenyl)-3,5-dihydro-2-methyl-furo[3,2-c][1,8]naphthyridin-4(2H)-one A solution of p-toluene sulfonic acid (5 g.) in toluene (100 ml.) was prepared. To this was added 1-(3,4-dichlorophenyl)-4-hydroxy-3-(2-hydroxypropyl)-1,8-naphthyridin-2(1H)-one (5 g.) and the mixture was stirred and heated to reflux in an atmosphere of nitrogen. The mixture was refluxed for 18 hrs. The resulting solution was poured into water (200 ml.), stirred for ½ hr. then filtered. The solids were recrystallized from isopropanol to yield the product, m.p. 273°–274° C.

EXAMPLE 5

2-n-Butyl-3,5-dihydro-5-phenyl-furo[3,2-c][1,8]naphthyridin-4(2H)-one

A solution of 4-hydroxy-3-(2-hydroxyhexyl)-1-phenyl-1,8-naphthyridin-2(1H)-one (2 g.) in 47% HBr was stirred in an atmosphere of nitrogen and heated to 80° C. for 4½ hrs. after which time it was cooled and poured into water. The precipitate was filtered off, washed with water, dried in air, recrystallized from ethanol/charcoal to yield the product m.p. 179°–180° C.

EXAMPLE 6

2-Methyl-3,5-dihydro-5-phenyl-furo[3,2-c][1,8]naphthyridin-4(2H)-one

A solution of 4-hydroxy-3-(2-hydroxypropyl)-1-phenyl-1,8-naphthyridin-2(1H)-one (8.9 g; 0.03 mole) in 47% HBr (90 ml.) was stirred in an atmosphere of nitrogen. The solution was heated to 90° C. for 4½ hrs. then was allowed to cool, poured into water and was adjusted to pH 4.5 with sodium acetate. The product was filtered off, washed with water, dried in air and recrystallized from CHCl$_3$/isopropanol to yield the product, m.p. 223°–224° C.

EXAMPLE 7

6-Phenyl-2,3,4,6-tetrahydro-pyrano[3,2-c][1,8]naphthyridin-5-one

A suspension of 4-hydroxy-3-(3-hydroxypropyl)-1-phenyl-1,8-naphthyridin-2(1H)-one (5.67 g.) in 47% HBr (50 ml.) was stirred in an atmosphere of nitrogen and was heated to 90° C. for 5 hrs. After cooling, the product was poured into water, and the pH was adjusted to 4.5 with potassium acetate. Chromatographic purification of the product on silica gel eluting with CH$_2$Cl$_2$: 5% ether and subsequent recrystallization of the product from the relevant fractions yielded the product, m.p. 253°–255° C.

EXAMPLE 8

3,5-Dihydro-5-phenyl-furo[3,2-c][1,8]naphthyridin-4(2H)-one

A solution of 4-hydroxy-3-(2-hydroxyethyl)-1-phenyl-1,8-naphthyridin-2-(1H)-one (10 g.) in 30% (v/v) sulfuric acid (200 ml.) was heated to reflux, in an atmosphere of nitrogen, and was held at reflux until no further reaction occured (ca. 5–8 hrs.). After cooling, the solution was added slowly and carefully to an ice-cooled solution of sodium hydroxide (50% solution; 200 ml.). The mixture was allowed to stand overnight and was then filtered. The product was washed with water, dried in air and recrystallized from dimethylformamide/water, with charcoal treatment, to yield the product, m.p. 276°–277.5° C.

The following compounds may be similarly prepared by substituting the appropriate starting material and using the method of Examples 5, 6, 7 or 8.

3,5-Dihydro-5-(4-chlorophenyl)-furo[3,2-c][1,8]naphthyridin-4(2 H)-one, m.p. 260° C.
3,5-Dihydro-2-methyl-5-(4-chlorophenyl)-furo[3,2-c][1,8]naphthyridin-4(2 H)-one
3,5-Dihydro-2-ethyl-5-(4-chlorophenyl)-furo[3,2-c][1,8]naphthyridin-4(2H)-one
3,5-Dihydro-2-(n-propyl)-5-(4-chlorophenyl)furo[3,2-c][1,8]naphthyridin-4(2H)-one
3,5-Dihydro-2-(n-butyl)-5-(4-chlorophenyl)furo[3,2-c][1,8]naphthyridin-4(2H)-one
3,5-Dihydro-2-ethyl-5-phenyl-furo[3,2-c][1,8]naphthyridin-4(2 H)-one
3,5-Dihydro-2-(n-propyl)-5-phenyl-furo[3,2-c][1,8]naphthyridin-4(2 H)-one
3,5-Dihydro-2-(iso-butyl)-5-phenyl-furo[3,2-c][1,8]naphthyridin-4(2 H)-one
3,5-Dihydro-2,2-dimethyl-5-phenyl-furo[3,2-c][1,8]naphthyridin-4(2H)-one, m.p. 216°–217.5° C.
3,5-Dihydro-5-(4-fluorophenyl)-furo[3,2-c][1,8]naphthyridin-4(2H)-one, m.p. 260° C.
3,5-Dihydro-2-methyl-5-(4-fluorophenyl)-furo[3,2-c][1,8]naphthyridin-4(2H)-one, m.p. 252°–254° C.
3,5-Dihydro-2-ethyl-5-(4-fluorophenyl)-furo[3,2-c][1,8]naphthyridin-4(2H)-one
3,5-Dihydro-2-(n-propyl)-5-(4-fluorophenyl)furo-[3,2-c][1,8]naphthyridin-4(2H)-one
3,5-Dihydro-2-(n-butyl)-5-(4-fluorophenyl)-furo-[3,2-c][1,8]naphthyridin-4(2H)-one
3,5-Dihydro-5-(4-methylphenyl)-furo[3,2-c][1,8]naphthyridin-4(2H)-one, m.p. 258.5°–260° C.
3,5-Dihydro-2-methyl-5-(4-methylphenyl)-furo[3,2-c][1,8]naphthyridin-4(2H)-one
3,5-Dihydro-2-(n-butyl)-5-(4-methylphenyl)-furo[3,2-c][1,8]naphthyridin-4(2H)-one
3,5-Dihydro-5-(4-methoxyphenyl)-furo[3,2-c][1,8]naphthyridin-4(2H)-one, m.p. 282°–284° C.
3,5-Dihydro-2-methyl-5-(4-methoxyphenyl)-furo[3,2-c][1,8]naphthyridin-4(2H)-one
3,5-Dihydro-2-(n-butyl)-5-(4-methoxyphenyl)-furo[3,2-c][1,8]naphthyridin-4(2H)-one
3,5-Dihydro-5-(3,4-dichlorophenyl)-furo[3,2-c][1,8]naphthyridin-4(2H)-one, m.p. 256.5°–258° C.
3,5-Dihydro-2-methyl-5-(3,4-dichlorophenyl)-furo[3,2-c][1,8]naphthyridin-4(2H)-one, 273°–274° C.
3,5-Dihydro-2-(n-butyl)-5-(3,4-dichlorophenyl)-furo[3,2-c][1,8]naphthyridin-4(2H)-one
3,5-Dihydro-5-(3-methoxyphenyl)-furo[3,2-c][1,8]naphthyridin-4(2H)-one
3,5-Dihydro-2-methyl-5-(3-methoxyphenyl)-furo[3,2-c][1,8]naphthyridin-4(2H)-one, m.p. 260° C.
3,5-Dihydro-2-(n-butyl)-5-(3-methoxyphenyl)-furo[3,2-c][1,8]naphthyridin-4(2H)-one
3,5-Dihydro-5-(3-methylmercaptophenyl)-furo[3,2-C][1,8]naphthyridin-4(2H)-one-
3,5-Dihydro-2-methyl-5-(3-methylmercaptophenyl)-furo[3,2-c][1,8]naphthyridin-4(2H)-one
3,5-Dihydro-2-(n-butyl)-5-(3-methylmercaptophenyl)-furo[3,2-c][1,8]naphthyridin-4(2H)-one
3,5-Dihydro-5-(3-methylsulfinylphenyl)-furo[3,2-c][1,8]naphthyridin-4(2H)-one
3,5-Dihydro-2-methyl-5-(3-methylsulfinylphenyl)-furo[3,2-c][1,8]naphthyridin-4(2H)-one
3,5-Dihydro-2-(n-butyl)-5-(3-methylsulfinylphenyl)-furo[3,2-c][1,8]naphthyridin-4(2H)-one
3,5-Dihydro-5-(3-methylsulfonylphenyl)-furo[3,2-c][1,8]naphthyridin-4(2H)-one
3,5-Dihydro-2-methyl-5-(3-methylsulfonylphenyl)-furo[3,2-c][1,8]naphthyridin-4(2H)-one
3,5-Dihydro-2-(n-butyl)-5-(3-methylsulfonylphenyl)-furo[3,2-c][1,8]naphthyridin-4(2H)-one
3,5-Dihydro-5-(3,5-dichlorophenyl)-furo[3,2-c][1,8]naphthyridin-4(2H)-one, m.p. 283°–284° C.
3,5-Dihydro-2-methyl-5-(3,5-dichlorophenyl-furo[3,2-c][1,8]naphthyridin-4(2H)-one, m.p. 254°–256° C.
3,5-Dihydro-5-(2,3-dichlorophenyl)-furo[3,2-c][1,8]naphthyridin-4(2H)-one 3,5-Dihydro-2-methyl-5-(2,3-dichlorophenyl)furo[3,2-c][1,8]naphthyridin-4(2H)-one
3,5-Dihydro-5-(2,5-dichlorophenyl)furo[3,2-c][1,8]naphthyridin-4(2H)-one
3,5-Dihydro-2-methyl-5-(2,5-dichlorophenyl)furo[3,2-C][3,2-c][1,8]naphthyridin-4(2H-one
3,5-Dihydro-5-(3-chloro-4-fluorophenyl)-furo][1,8-]naphthyridin-4(2H)-one
3,5-Dihydro-2-methyl-5-(3-chloro-4-fluoro phenyl)-furo[3,2-c][1,8]naphthyridin-4(2H)-one
3,5-Dihydro-2-methyl-5-(3-trifluoromethylphenyl)-furo[3,2-c][1,8]naphthyridin-4(2H)-one
3,5-Dihydro-2-methyl-5-(3-trifluoromethylphenyl)-furo[3,2-c][1,8]naphthyridin-4(2H)-one
3,5-Dihydro-5-(3-chlorophenyl)-furo[3,2-c][1,8]-naphthyridin-4(2H)-one, m.p. 205°-207° C.
3,5-Dihydro-2-methyl-5-(3-chlorophenyl)-furo[3,2-C][1,8]naphthyridin-4(2H)-one, m.p. 254°-256° C.
3,5-Dihydro-5-benzyl-furo[3,2-c][1,8]naphthyridin-4(2H)-one
3,5-Dihydro-2-methyl-5-benzyl-furo[3,2-c][1,8]naphthyridin-4(2H)-one
3,5-Dihydro-5-(2-phenylethyl)-furo[3,2-c][1,8]naphthyridin-4(2H)-one
3,5-Dihydro-2-methyl-5-(2-phenylethyl)-furo[3,2-C[1,8]naphthyridin-4(2H)-one
3,5-Dihydro-5-(1-phenylethyl)-furo[3,2-c][1,8]naphthyridin-4(2H)-one
3,5-Dihydro-2-methyl-5-(1-phenylethyl)-furo[3,2-c][1,8]naphthyridin-4(2H)-one
3,5-Dihydro-5-(2-thienylmethyl)-furo[3,2-c][1,8]naphthyridin-4(2H)-one
3,5-Dihydro-2-methyl-5-(2-thienylmethyl)-furo[3,2-c][1,8]naphthyridin-4(2H)-one
3,5-Dihydro-5-(2-thiazolyl)-furo[3,2-c][1,8]naphthyridin-4(2H)-one
3,5-Dihydro-2-methyl-5-(2-thiazolyl)-furo[3,2-c][1,8]naphthyridin-4(2H)-one
3,5-Dihydro-5-(2-pyridyl)-furo[3,2-c][1,8]naphthyridin-4(2H)-one
3,5-Dihydro-5-[2-(2-pyridyl)ethyl]-furo[3,2-c][1,8]naphthyridin-4(2H)-one
3,5-Dihydro-2-methyl-5-(3-methylsulfonylamino phenyl)-furo[3,2-c][1,8]naphthyridin-4[2H]-one, m.p. 258°-260° C.
3,5-Dihydro-5-(3-methylsulfonylaminophenyl)-furo[3,2-C]1,8]-naphthyridin-4[2H]-one, m.p. 260° C.
3,5-Dihydro-5-phenyl-furo[3,2-c]quinolin-4(2H)-one
3,5-Dihydro-2-methyl-5-phenyl-furo[3,2-c]quinolin-4(2H)-one, m.p. 195°-197° C.
3,5-Dihydro-2-(n-butyl)-5-phenyl-furo[3,2-c]quinolin-4(2H)-one
3,5-Dihydro-8-chloro-5-phenyl-furo[3,2-c]quinolin-4(2H)-one
3,5-Dihydro-2-methyl-8-chloro-5-phenyl-furo[3,2-c]quinolin-4(2H)-one
3,5-Dihydro-8-fluoro-5-phenyl-furo[3,2-c]quinolin-4(2H)-one
3,5-Dihydro-2-methyl-8-fluoro-5-phenyl-furo[3,2-c]quinolin-4(2H)-one
3,5-Dihydro-8-methoxy-5-phenyl-furo[3,2-c]quinolin-4(2H)-one
3,5-Dihydro-2-methyl-8-methoxy-5-phenyl-furo[3,2-c]quinolin-4(2H)-one
3,5-Dihydro-7-chloro-5-phenyl-furo[3,2-c]quinolin-4(2H)-one
3,5-Dihydro-2-methyl-7-chloro-5-phenyl-furo[3,2-c]quinolin-4(2H)-one
3,5-Dihydro-7-fluoro-5-phenyl-furo[3,2-c]quinolin-4(2H)-one
3,5-Dihydro-2-methyl-7-fluoro-5-phenyl-furo[3,2-c]quinolin-4(2H)-one
3,5-Dihydro-5-(4-fluorophenyl)furo[3,2-c]quinolin-4(2H)-one
3,5-Dihydro-2-methyl-5-(4-fluorophenyl)-furo[3,2-c]quinolin-4(2H)-one
3,5-Dihydro-5-(3-methoxyphenyl)-furo[3,2-c]quinolin-4(2H)-one
3,5-Dihydro-2-methyl-5-(3-methoxyphenyl)-furo[3,2-c]quinolin-4(2H)-one
3,5-Dihydro-5-(3-methylmercaptophenyl)-furo-[3,2-c]quinolin-4(2H)-one
3,5-Dihydro-2-methyl-5-(3-methylmercaptophenyl)furo[3,2-c]quinolin-4(2H)-one
3,5-Dihydro-5-(3,5-dichlorophenyl)-furo[3,2-c]quinolin-4(2H)-one
3,5-Dihydro-2-methyl-5-(3,5-dichlorophenyl)furo[3,2-c]quinolin-4(2H)-one
3,5-Dihydro-2-methyl-5-(3-chlorophenyl)-furo[3,2-c]quinolin-4(2H)-one
3,5-Dihydro-5-(3-chlorophenyl)-furo[3,2-c]quinolin-4(2H)-one
3,5-Dihydro-5-(3-trifluoromethylphenyl)-furo[3,2-c]quinolin-4(2H)-one
3,5-Dihydro-2-methyl-5-(3-trifluoromethylphenyl)-furo[3,2-c]quinolin-4(2H)-one
3,5-Dihydro-5-(3-chloro-4-fluorophenyl)-furo[3,2-c]quinolin-4(2H)-one
3,5-Dihydro-2-methyl-5-(3-chloro-4-fluorophenyl)-furo[3,2-c]quinolin-4(2H)-one
3,5-Dihydro-5-benzyl-furo[3,2-c]quinolin-4(2H)-one
3,5-Dihydro-2-methyl-5-benzyl-furo[3,2-c]quinolin-4(2H)-one
3,5-Dihydro-5-(2-phenylethyl)-furo[3,2-c]quinolin-4(2H)-one
3,5-Dihydro-5-(2-thienylmethyl)-furo[3,2-c]quinolin-4(2H)-one
3,5-Dihydro-5-(2-pyridyl)-furo[3,2-c]quinolin-4(2H)-one
3,5-Dihydro-[2-(2-pyridyl)ethyl]-5-furo[3,2-c]quinolin-4(2H)-one
2,3,4,6-Tetrahydro-6-phenyl-pyrano[3,2-c][1,8]naphthyridin-5-one, m.p. 253°-255° C.
2,3,4,6-Tetrahydro-2-methyl-6-phenyl-pyrano[3,2-c][1,8]naphthyridin-5-one
2,3,4,6-Tetrahydro-6-(4-fluorophenyl)-pyrano[3,2-c][1,8]naphthyridin-5-one
2,3,4,6-Tetrahydro-6-(4-chlorophenyl)-pyrano[3,2-c][1,8]naphthyridin-5-one, m.p. 236°-237° C.
2,3,4,6-Tetrahydro-6-(3,4-dichlorophenyl)pyrano[3,2-c][1,8]naphthyridin-5-one, m.p. 265° C.
2,3,4,6-Tetrahydro-6-(4-methylphenyl)-pyrano[3,2-C][1,8]naphthyridin-5-one, m.p. 280° C.
2,3,4,6-Tetrahydro-6-(4-methoxyphenyl)-pyrano[3,2-c][1,8]naphthyridin-5-one, m.p. 270° C.
2,3,4,6-Tetrahydro-6-(3-methoxyphenyl)-pyrano[3,2-c][1,8]naphthyridin-5-one
2,3,4,6-Tetrahydro-6-(3-chlorophenyl)-pyrano[3,2-c][1,8]naphthyridin-5-one
2,3,4,6-Tetrahydro-6-(3-methylmercaptophenyl)-pyrano[3,2-c][1,8]naphthyridin-5-one
2,3,4,6-Tetrahydro-6-(3,5-dichlorophenyl)pyrano-[3,2-c][1,8]naphthyridin-5-one
2,3,4,6-Tetrahydro-6-(2,3-dichlorophenyl)-pyrano[3,2-c][1,8]naphthyridin-5-one 2,3,4,6-Tetrahydro-6-(2,5-dichlorophenyl)-pyrano[3,2-c][1,8]naphthyridin-5-one
2,3,4,6-Tetrahydro-6-(3-chloro-4-fluorophenyl)-pyrano[3,2-c][1,8]naphthyridin-5-one
2,3,4,6-Tetrahydro-6-(3-trifluoromethylphenyl)-pyrano[3,2-c][1,8]naphthyridin-5-one
2,3,4,6-Tetrahydro-6-benzyl-pyrano-[3,2-c][1,8]naphthyridin-5-one
2,3,4,6-Tetrahydro-6-(2-phenylethyl)-pyrano[3,2-c][1,8]naphthyridin-5-one
2,3,4,6-Tetrahydro-6-(2-thienylmethyl)-pyrano[3,2-c][1,8]naphthyridin-5-one
2,3,4,6-Tetrahydro-6-(2-thiazolyl)-pyrano[3,2-c][1,8]naphthyridin-5-one
2,3,4,6-Tetrahydro-6-(2-[2-pyridyl]ethyl-pyrano[3,2-c][1,8]naphthyridin-5-one
2,3,4,6-Tetrahydro-6-phenyl-pyrano[3,2-c]quinolin-5-one
2,3,4,6-Tetrahydro-2-methyl-6-phenyl-pyrano[3,2-c]quinolin-5-one
2,3,4,6-Tetrahydro-9-chloro-6-phenyl-pyrano[3,2-c]quinolin-5-one
2,3,4,6-Tetrahydro-9-fluoro-6-phenyl-pyrano[3,2-c]quinolin-5-one
2,3,4,6-Tetrahydro-9-methoxy-6-phenyl-pyrano[3,2-c]quinolin-5-one
2,3,4,6-Tetrahydro-9-methyl-6-phenyl-pyrano[3,2-c]quinolin-5-one
2,3,4,6-Tetrahydro-8-chloro-6-phenyl-pyrano[3,2-c]quinolin-5-one
2,3,4,6-Tetrahydro-8-fluoro-6-phenyl-pyrano[3,2-c]quinolin-5-one
2,3,4,6-Tetrahydro-8-methoxy-6-phenyl-pyrano[3,2-c]quinolin-5-one
2,3,4,6-Tetrahydro-6-(4-fluorophenyl)-pyrano[3,2-c]quinolin-5-one
2,3,4,6-Tetrahydro-6-(4-chlorophenyl)-pyrano[3,2-C]quinolin -5-one
2,3,4,6-Tetrahydro-6-(4-methoxyphenyl)-pyrano[3,2-c]quinolin-5-one
2,3,4,6-Tetrahydro-6-(3-chlorophenyl)-pyrano[3,2-c]quinolin-5-one
2,3,4,6-Tetrahydro-6-(3-methoxyphenyl)-pyrano[3,2-c]quinolin-5-one
2,3,4,6-Tetrahydro-6-(3-methylmercaptophenyl)-pyrano[3,2-c]quinolin-5-one
2,3,4,6-Tetrahydro-6-benzyl-pyrano-[3,2-c]quinolin-5-one
2,3,4,6-Tetrahydro-6-(2-phenylethyl)-pyrano[3,2-c]quinolin-5-one
2,3,4,6-Tetrahydro-6-(2-thienylmethyl)-pyrano[3,2-c]quinolin-5-one
2,3,4,6-Tetrahydro-6-(2-thiazolyl)-pyrano[3,2-c]quinolin-5-one
2,3,4,6-Tetrahydro-6-[2-(2-pyridyl)ethyl]pyrano[3,2-c]quinolin-5-one
3,5-Dihydro-5-phenyl-furo[3,2-c][1,5]naphthyridin-4(2H)-one
3,5-Dihydro-2-methyl-5-phenyl-furo[3,2-c][1,5]naphthyridin-4(2H)-one
3,5-Dihydro-2-ethyl-5-phenyl-furo[3,2-c][1,5]naphthyridin-4(2H)-one
3,5-Dihydro-2-(n-butyl)-5-phenyl-furo[3,2-c][1,5]naphthyridin-4(2H)-one
3,5-Dihydro-5-(4-chlorophenyl)-furo[3,2-c][1,5]-naphthyridin-4(2H)-one
3,5-Dihydro-2-methyl-5-(4-chlorophenyl)-furo[3,2-c][1,5]naphthyridin-4(2H)-one
3,5-Dihydro-5-(4-fluorophenyl)-furo[3,2-c][1,5]-naphthyridin-4(2H)-one
3,5-Dihydro-2-methyl-5-(4-fluorophenyl)-furo[3,2-C][1,5]naphthyridin-4(2H)-one
3,5-Dihydro-5-(4-methylphenyl)-furo-[3,2-c][1,5]-naphthyridin-4(2H)-one
3,5-Dihydro-5-(4-methoxyphenyl)-furo[3,2-c][1,5]naphthyridin-4(2H)-one
3,5-Dihydro-5-(3,4-dichlorophenyl)-furo[3,2-c][1,5]naphthyridin-4(2H)-one
3,5-Dihydro-5-(3-methoxyphenyl)-furo[3,2-c][1,5]naphthyridin-4(2H)-one
3,5-Dihydro-2-methyl-5-(3-methoxyphenyl)-furo[3,2-c][1,5]naphthyridin-4(2H)-one
3,5-Dihydro-5-(3-methylmercaptophenyl)-furo[3,2-c][1,5]naphthyridin-4(2H)-one
3,5-Dihydro-2-methyl-5-(3-methylmercaptophenyl)-furo[3,2-c][1,5]naphthyridin-4(2H)-one
3,5-Dihydro-5-(3-chlorophenyl)-furo[3,2-c][1,5]-naphthyridin-4(2H)-one
3,5-Dihydro-2-methyl-5-(3-chlorophenyl)-furo[3,2-C][1,5]naphthyridin-4(2H)-one
3,5-Dihydro-5-benzyl-furo[3,2-c][1,5]naphthyridin-4(2H)-one
3,5-Dihydro-5-(2-thienylmethyl)-furo[3,2-c][1,5]naphthyridin-4(2H)-one
3,5-Dihydro-5-(2-thiazolyl)-furo[3,2-c][1,5]naphthyridin-4(2H)-one
3,5-Dihydro-5-(2-pyridyl)-furo[3,2-c][1,5]naphthyridin-4(2H)-one
3,5-Dihydro-5-[2-(2-pyridyl)ethyl]-furo[3,2-C][1,5]naphthyridin-4(2H)-one
2,3,4,6-Tetrahydro-6-phenyl-pyrano[3,2-c][1,5]naphthyridin-5-one
2,3,4,6-Tetrahydro-2-methyl-6-phenyl-pyrano[3,2-c][1,5]naphthyridin-5-one
2,3,4,6-Tetrahydro-6-(4-fluorophenyl)-pyrano[3,2-c][1,5]naphthyridin-5-one
2,3,4,6-Tetrahydro-6-(4-chlorophenyl)-pyrano[3,2-c][1,5]naphthyridin-5-one
2,3,4,6-Tetrahydro-6-(3,4-dichlorophenyl)pyrano[3,2-c][1,5]naphthyridin-5-one
2,3,4,6-Tetrahydro-6-(4-methylphenyl)-pyrano[3,2-C][1,5]naphthyridin-5-one
2,3,4,6-Tetrahydro-6-(4-methoxyphenyl)-pyrano[3,2-c][1,5]naphthyridin-5-one
2,3,4,6-Tetrahydro-6-(3-methoxyphenyl)-pyrano[3,2-c][1,5]naphthyridin-5-one
2,3,4,6-Tetrahydro-6-(3-methylmercaptophenyl)-pyrano[3,2-c][1,5]naphthyridin-5-one
2,3,4,6-Tetrahydro-6-(3-chlorophenyl)-pyrano[3,2-c][1,5]naphthyridin-5-one
2,3,4,6-Tetrahydro-6-benzyl-pyrano-[3,2-c][1,5]naphthyridin-5-one
2,3,4,6-Tetrahydro-6-(2-phenylethyl)-pyrano[3,2-c][1,5]naphthyridin-5-one
2,3,4,6-Tetrahydro-6-(2-thienylmethyl)-pyrano[3,2-c][1,5]naphthyridin-5-one
2,3,4,6-Tetrahydro-6-(2-thiazolyl)-pyrano[3,2-c[]1,5]napthyridin--5-one
2,3,4,6-Tetrahydro-6-(2-[2-pyridyl]ethyl)pyrano[3,2-c][1,5]naphthyridin-5-one
7,8-Dihydro-5-phenyl-furo[2',3':4,5]pyrido[2,3-b]pyrazin-6(5H)-one
7,8-Dihydro-8-methyl-5-phenyl-furo[2',3':4,5]pyrido[2,3-b]pyrazin-6(5H)-one
7,8-Dihydro-8-(n-butyl)-5-phenyl-furo2',3':4,5]pyrido[2,3-b]pyrazin-6(5H)-one 7,8-Dihydro-5-(4-fluorophenyl)-furo[2',3':4,5-]pyrido[2,3-b]pyrazin-6(5H)-one
7,8-Dihydro-8-methyl-5-(4-fluorophenyl)-furo2',3':4,5-]pyrido[2,3-b]pyrazin-6(5H)-one
7,8-Dihydro-2,3-dimethyl-5-(4-fluorophenyl)-furo[2',3':4,5]pyrido[2,3-b]pyrazin-6(5H)-one
7,8-Dihydro-2,3,8-trimethyl-5-(4-fluorophenyl)-furo[2',3':4,5]pyrido[2,3-b]pyrazin-6(5H)-one
7,8-Dihydro-5-(4-chlorophenyl)-furo[2',3':4,5-]pyrido[2,3-b]pyrazin-6(5H)-one
7,8-Dihydro-5-(4-methylphenyl)-furo[2',3':4,5-]pyrido[2,3-b]pyrazin-6(5H)-one
7,8-Dihydro-5-(4-methoxyphenyl)-furo[2',3':4,5]-pyrido[2,3-b]pyrazin-6(5H)-one
7,8-Dihydro-5-(3-methoxyphenyl)-furo[2',3':4,5]-pyrido[2,3-b]pyrazin-6(5H)-one
7,8-Dihydro-8-methyl-5-(3-methoxyphenyl)-furo[2',3':4,5]pyrido[2,3-b]pyrazin-6(5H)-one
7,8-Dihydro-2,3-dimethyl-5-(3-methoxyphenyl)-furo[2',3':4,5]pyrido[2,3-b]pyrazin-6(5H)-one
7,8-Dihydro-5-(3-methylmercaptophenyl)-furo[2',3':4,5]pyrido[2,3-b]pyrazin-6(5H)-one
7,8-Dihydro-8-methyl-5-(3-methylmercaptophenyl)-furo[2',3':4,5]pyrido[2,3-b]pyrazin-6(5H)-one
7,8-Dihydro-2,3-dimethyl-5-(3-methylmercaptophenyl)-furo[2',3':4,5]pyrido[2,3-b]pyrazin-6(5H)-one
7,8-Dihydro-5-(3-chlorophenyl)-furo[2',3':4,5]-pyrido[2,3-b]pyrazin-6(5H)-one
7,8-Dihydro-8-methyl-5-(3-chlorophenyl)-furo[2',3':4,5]pyrido[2,3-b]pyrazin-6(5H)-one
7,8-Dihydro-2,3-dimethyl-5-(3-chlorophenyl)-furo-[2',3':4,5]pyrido[2,3-b]pyrazin-6(5H)-one
5,7,8,9-Tetrahydro-5-phenyl-6H-pyrano[2',3':4,5-]pyrido[2,3-b]pyrazin-6-one
5,7,8,9-Tetrahydro-9-methyl-5-phenyl-6H-pyrano[2',3':4,5]pyrido[2,3-b]pyrazin-6-one
5,7,8,9-Tetrahydro-5-(4-fluorophenyl)-6H-pyrano-[2',3':4,5]pyrido[2,3-b]pyrazin-6-one
5,7,8,9-Tetrahydro-2,3-dimethyl-5-(4-fluorophenyl)-6H-pyrano-[2',3':4,5]pyrido[2,3-b]pyrazin-one
5,7,8,9-Tetrahydro-5-(4-chlorophenyl) -6H-pyrano-[2',3':4,5]pyrido[2,3-b]pyrazin-6-one
5,7,8,9-Tetrahydro-5-(4-methylphenyl)-6H- pyrano-[2',3':4,5]pyrido[2,3-b]pyrazin-6-one
5,7,8,9-Tetrahydro-5-(4-methoxyphenyl)-6H-pyrano[2',3':4,5]pyrido[2,3-b]pyrazin-6-one
5,7,8,9-Tetrahydro-5-(3-methoxyphenyl)-6H-pyrano[2',3':4,5]pyrido[2,3-b]pyrazin-6-one
5,7,8,9-Tetrahydro-2,3-dimethyl-5-(4-fluorophenyl)-6H-pyrano-[2',3':4,5]pyrido[2,3-b]pyrazin-6-one
5,7,8,9-Tetrahydro-5-(3-methylmercaptophenyl)-6H-pyrano[2',3':4,5]pyrido[2,3-b]pyrazin-6-one
5,7,8,9-Tetrahydro-2,3-dimethyl-5-(4-fluorophenyl)-6H-pyrano-[2',3':4,5]pyrido[2,3-b]pyrazin-6-one
5,7,8,9-Tetrahydro-5-(3-chlorophenyl)-6H-pyrano-[2',3':4,5]pyrido[2,3-b]pyrazin-6-one
5,7,8,9-Tetrahydro-2,3-dimethyl-5-(3-chloro-phenyl)-6H-pyrano-[2',3':4,5]pyrido[2,3-b]pyrazin-6-one

EXAMPLE 9

5-(3,4-Dichlorophenyl)-3,5-dihydro-2-methyl-furo[3,2-c][1,8]naphthyridin-4(2H)-one To a solution of 9-(3,4-dichlorophenyl)-3,9-dihydro-2-methyl-furo[2,3-b][1,8]naphthyridin-4(2H)-one (125 mg.) (prepared as in example 2) in dimethylacetamide (20 ml.) in an atmosphere of nitrogen was added sodium iodide (250 mg.). The solution was refluxed for 4 hrs., and it was poured over ice-water, filtered, dried and recrystallized from isopropanol to yield the desired product, m.p. 273°–274° C.

EXAMPLE 10

A mixture of 4-hydroxy-3-(2'-hydroxyethyl) 1-phenyl-1, 8-naphthyridin-2(1H)-one (3 g.) and 2,4-bis (4-methoxyphenyl)-1,3-dithia-2,4-diphosphetane-2,4-disulfide (also known as Lawesson's Reagent) (4.3 g.) in toluene (100 ml) was stirred in an atmosphere of nitrogen and heated to reflux. The mixture was refluxed for 20 hr. after which it was cooled, evaporated, dissolved in $CH_2Cl_2$, washed with water, dried, and chromatographed over silica gel, eluting with increasing concentrations of ethyl acetate (0–5%) in $CH_2Cl_2$. Three products were isolated and characterised as follows:
1st compound eluted:
3,5-Dihydro-5-phenyl-thieno[3,2-c][1,8]naphthyridin-4[2H]-thione, m.p. 275°–276.5° C.
2nd compound eluted:
3,5-Dihydro-5-phenyl-furo[3,2-c][1,8]naphthyridin-4[2H]-thione, m.p. 243°–245.5° C.
3rd compound eluted:
3,9-Dihydro-9-phenyl-thieno[2,3-b][1,8]naphthyridin-4[2H]-thione, m.p. 264°–266° C. (dec)

In a similar manner, application of this procedure to other compounds having structural formula II would lead to the preparation of analogous products to those described in this Example.

EXAMPLE 11

3,5-Dihydro-5-(4-methoxyphenyl)-furo-[3,2-c][1,8]naphthyridin-4(2H)-one

A solution of 3,9-dihydro-9-(4-methoxyphenyl)-furo[2,3-b][1,8]naphthyridin-4(2H)-one (1 g.) and sodium iodide (1 g.) in dry dimethylacetamide (10 ml.) was heated to 70° C. for 4 hr in a nitrogen atmosphere. The product was cooled, poured over ice-water, filtered, dried and recrystallized from $CH_2Cl_2$ to yield the desired product, m.p. 282°–284° C.

Essentially any of the products, prepared according to the procedures of Examples 1 and 2, and in which a methylene group is next to the ring oxygen atom may be converted by this process into the products which may otherwise be prepared according to the procedures of Examples 5, 6, 7 and 8.

EXAMPLE 12

3,5-Dihydro-5-phenyl-furo[3,2-c][1,8]-naphthyridine-4(2H)-thione

A suspension of 3,5-dihydro-5-phenyl-furo-[3,2-c][1,8]naphthyridin-4(2H)-one (3 g.) and 2,4-bis- (4-methoxyphenyl)-1,3-dithia-2,4-diphosphetane-2,4-disulfide (Lawesson's Reagent; 5 g.) in dry toluene (100 ml.) was stirred in an atmosphere of nitrogen and heated to reflux for 6 hrs. After cooling, the organic layer was washed with water, dried and evaporated. The product was purified by chromatography over silica gel in $CH_2Cl_2$ containing increasing amounts of ethyl acetate (0–5%). The fractions containing pure product were combined, evaporated, suspended in ethanol, filtered and dried to yield the desired product, m.p. 242°–244.5° C.

In a similar manner, other compounds produced according to Examples 5, 6, 7 or 8 may be converted to their thione analogs by this process.

EXAMPLE 13

3,9-Dihydro-9-phenyl-thieno[2,3-b][1,8]-naphthyridin-4(2H)-one

A solution of 3,5-dihydro-5-phenyl-furo-[3,2-c]-[1,8]naphthyridin-4(2H)-thione (500 mg.) and sodium iodide (500 mg.) in dry dimethylacetamide (5 ml.) was stirred in an atmosphere of nitrogen and heated at 125° for 2 hr. After cooling, the solution was poured into ice-water, filtered, washed with water and dried to yield the desired product, m.p. 260°–261° C.

Similarly may be prepared other such derivatives from the corresponding starting materials prepared according to the method of Example 12.

EXAMPLE 14

5-Phenyl-furo[3,2-c][1,8]naphthyridin-4[5H]-one

A mixture of 3,5-dihydro-5-phenyl-furo-[3,2-c][1,8]naphthyridin-4[2H]-one (2 g.) and 2,3-dichloro-5,6-dicyano-1,4-benzoquinone (DDQ; 2 g.) in dry toluene (50 ml.) was stirred in an atmosphere of nitrogen and heated to reflux. Refluxing was continued for 20 hrs. After cooling somewhat the mixture was evaporated, dissolved in $CH_2Cl_2$, filtered and chromatographed on silica gel eluting with increasing concentrations of ethyl acetate in $CH_2Cl_2$ (0–10%). Evaporation of the relevant fractions and recrystallization from acetonitrile yielded the desired product, m.p. 245°–247° C.

In a similar manner, any of the tricyclic-dihydro-furo derivatives may be oxidized to the corresponding furo-derivative.

EXAMPLE 15

3,9-Dihydro-9-phenyl-furo[2,3-b][1,8]-naphthyridin-4(2H)-thione

To a stirred suspension of 3,9-dihydro-9-phenyl-furo[2,3-b][1,8]naphthyridin-4(2H)-one(1 g.) in dry toluene (40 ml.) at 55° C., under an atmosphere of dry nitrogen, was added a suspension of 2,4-bis,(4-methoxyphenyl)-1,3-dithia-2,4-diphosphetane-2,4-disulfide (Lawesson's Reagent; 0.8 g) in dry toluene (10 ml.). The reaction was followed by t.l.c. (silica gel/$CH_2Cl_2$:5% Methanol) and warming was continued until no starting material remained (ca. 2½ hr.). Toluene was removed under reduced pressure and the product was dissolved in $CH_2Cl_2$. The solution was separated by chromatography on silica gel eluting with increasing concentrations of ethyl acetate in $CH_2Cl_2$ (2%–5%). The desired product was obtained as an orange-yellow solid, m.p. ca. 273°–275° C. (dec.).

Similarly, application of this procedure to other compounds having structural formula I'', prepared according to the procedures of Examples 1 or 2, will produce the thione analogs of compounds described in those examples.

EXAMPLE 16

3,5-Dihydro-5-phenyl-thieno[3,2-c][1,8]-naphthyridin-4(2H)-one

A solution of 3,5-dihydro-9-phenyl-furo[2,3-b][1,8]-naphthyridin-4[2H]-thione (500 mg.) and sodium iodide (500 mg.) in dry dimethylacetamide (5 ml.) was stirred in an atmosphere of nitrogen and heated to 100° C. for 2 hrs. After cooling, the solution was poured into ice water, filtered, washed with water dried and recrystallized from isopropanol to yield the desired product, m.p. 277°–279° C.

In a similar manner may be prepared other such derivatives from the corresponding starting materials prepared according to the method of Example 15.

Examples of such compounds are:

3,5-Dihydro-2-methyl-5-phenyl-thieno[3,2-c][1,8]-naphthyridin-4(2H)-one 3,5-Dihydro-5-(4-fluorophenyl)-thieno[3,2-c][1,8]-naphthyridin-4(2H)-one 3,5-Dihydro-2-methyl-5-(4-fluorophenyl)-thieno[3,2-c][1,8]naphthyridin-4(2H)-one 3,5-Dihydro-5-(3-chlorophenyl)-thieno[3,2-c][1,8]-naphthyridin-4(2H)-one 3,5-Dihydro-2-methyl-5-(3-chlorophenyl)-thieno[3,2-c][1,8]naphthyridin-4(2H)-one 3,5-Dihydro-5-(3-methoxyphenyl)-thieno[3,2-c[1,8]-naphthyridin-4(2H)-one 3,5-Dihydro-2-methyl-5-(3-methoxyphenyl)-thieno-[3,2-c][1,8]naphthyridin-4(2H)-one-

3,5-Dihydro-5-(3-methylthiophenyl)-thieno[3,2-c][1,8]naphthyridin-4(2H)-one

3,5-Dihydro-2-methyl-5-(3-methylthiophenyl)-thieno[3,2-c][1,8]naphthyridin-4(2H)-one 3,5-Dihydro-5-(3-trifluoromethylphenyl)-thieno[3,2-c][1,8]naphthyridin-4(2H)-one 3,5-Dihydro-2-methyl-5-(3-trifluoromethylphenyl)-thieno[3,2-c][1,8]naphthyridin-4(2H)-one 3,5-Dihydro-5-(3,5-dichlorophenyl)-thieno[3,2-c][1,8]naphthyridin-4(2H)-one 3,5-Dihydro-2-methyl-5-(3,5-dichlorophenyl)-thieno-[3,2-c][1,8]naphthyridin-4(2H)-one 3,5-Dihydro-5-(3-chloro-4 -fluorophenyl)-thieno-[3,2-c][1,8]naphthyridin-4(2H)-one 3,5-Dihydro-2-methyl-5-(3-chloro-4-fluorophenyl)-thieno[3,2-c][1,8]naphthyridin-4(2H)-one 3,5-Dihydro-5-(4-chlorophenyl)-thieno[3,2-c][1,8]-naphthyridin-4(2H)-one 3,5-Dihydro-5-(4-methylphenyl)-thieno[3,2-c][1,8]-naphthyridin-4(2H)-one 3,5-Dihydro-5-(4-methoxyphenyl)-thieno[3,2-c][1,8]-naphthyridin-4(2H)-one 3,5-Dihydro-5-(3,4-dichlorophenyl)-thieno[3,2-c][1,8]naphthyridin-4(2H)-one 3,5-Dihydro-5-(3-methylsulfinylphenyl)-thieno[3,2-c][1,8]naphthyridin-4(2H)-one 3,5-Dihydro-5-(3-methylsulfonylphenyl)-thieno[3,2-c][1,8]naphthyridin-4(2H)-one

EXAMPLE 17

7-Phenyl-3,4,5,7-tetrahydro-oxepino[3,2-c][1,8]naphthyridin-6(2H)-one

The mono-mesylate (1 g.) from Preparative Example 7 was dissolved in DMF (20 ml.) at R.T. and cesium carbonate (2 g.) was added. The reaction was followed by HPLC or TLC until essentially no starting material remained (ca. 1 hr.). A mixture of two products was formed. The total product was poured into ice/water and the product was filtered off. The two products were separated by column chromatography [Whatman LPS-2 silica gel; $CH_2Cl_2$+0–5% MeOH] or by preparative reversed-phase HPLC [Whatman Partisil 40; ODS-3; Magnum 40 column] and the desired fractions isolated. Evaporation yielded 7-phenyl-3,4,5,7-tetrahydro-oxepino[3,2-c][1,8]naphthyridin-6(2H)-one m.p. 180°–181° C.

The following compounds may be prepared similarly by substituting the appropriate starting material from Preparative Example 6.

7-(3-Aminophenyl)-3,4,5,7-tetrahydro-oxepino-[3,2-c][1,9]-naphthyridin-6(2H)-one;

7-(3-Methylsulfonylaminophenyl)-3,4,5,7-tetrahydro-oxepino-[3,2-c][1,9]-naphthyridin-6(2H)-one;

7-(3-Formylaminophenyl)-3,4,5,7-tetrahydro-oxepino-[3,2-c][1,9]-naphthyridin-6(2H)-one;

7-(3-Acetylaminophenyl)-3,4,5,7-tetrahydro-oxepino-[3,2-c][1,9]-naphthyridin-6(2H)-one;

7-(3-Oxalylaminophenyl)-3,4,5,7-tetrahydro-oxepino-[3,2-c][1,9]-naphthyridin-6(2H)-one;

7-(4-Chlorophenyl)-3,4,5,7-tetrahydro-oxepino[3,2-c]1,8]naphthyridin-6(2H)-one, m.p. 241°–243° C.;

7-(3-Chlorophenyl)-3,4,5,7-tetrahydro-oxepino[3,2-c][1,8]naphthyridin-6(2H)-one, m.p. 151°–153° C.;

7-(3-Methoxyphenyl)-3,4,5,7-tetrahydro-oxepino[3,2-c][1,8]naphthyridin-6(2H)-one, m.p. 223°–224.5° C.; and 7-(3-Hydroxyphenyl)-3,4,5,7-tetrahydro-oxepino[3,2-c][1,8]naphthyridin-6(2H)-one, m.p. 260° C.

PREPARATIVE EXAMPLES

PREPARATIVE EXAMPLE 1

3-2-Hydroxyethyl)-4-hydroxy-1-phenyl-1,8-naphthyridin-2(1H)one

To a solution of 6.8 g. of methyl 2-phenyl-amino-3-pyridine carboxylate in 60 ml. of gamma-butyrolactone there was added, under nitrogen, 13.4 g. of potassium tertiary butoxide. The reaction mixture was heated and stirred for one hour at 95° C., poured on ice and stirred overnight. The mixture was extracted with ether, the aqueous layer acidified with acetic acid to pH 4.5 and the product was collected by filtration. Recrystallization from chloroform, acetone, isopropanol yielded the product of this example as a colorless solid; m.p. 235°–236° C.

According to this procedure, or an art-recognized modification thereof, any of the 2-hydroxyethyl side-chain materials used as starting materials in the reactions described in Examples 1–8 may be prepared.

PREPARATIVE EXAMPLE 2

Methyl-2-phenylamino-3-pyrazine carboxylate (A) Methyl 2-bromo-3-pyrazine carboxylate:

To a stirred mixture of 12.7 g. of methyl-2-amino pyrazine carboxylate and 47 ml. of 48% hydrobromic acid there was added, dropwise, 12.6 ml. of bromine keeping the temperature at 0°. A solution of 14.4 g. of sodium nitrite in 60 ml. of water was then added, dropwise, at 0° and the reaction mixture stirred for 15 minutes. The reaction mixture was basified to pH 8 with sodium bicarbonate and extracted with ethyl acetate and again with chloroform. The organic layers were dried over magnesium sulfate, filtered and concentrated to a yellow oil. Recrystallization from ether-hexane yielded the product, m.p. 43°–45° C.

(B) Methyl 2-phenylamino-3-pyrazine carboxylate:

A mixture of 9.5 g. of methyl 2-bromo-3-pyrazine carboxylate, 8.2 g. of aniline, 0.5 g. of p-toluene sulfonic acid and 100 ml. of water was stirred and refluxed for two hours. The reaction mixture was poured on ice, extracted with ethyl acetate, the organic extracts were dried and concentrated to yield an oil. The crude residue was eluted on a silica gel column with ethyl acetate-hexane (1:2) yielding the product of this example as a yellow solid, m.p. 72°–75° C.

PREPARATIVE EXAMPLE 3

4-Hydroxy-3-(3-hydroxypropyl)-1-(4-methoxyphenyl)-1,8-naphthyridin-2(1H)-one

A mixture of delta-valerolactone (120 ml.), ethyl 2-(4-methoxyphenylamino)nicotinate (12 g.) and potassium t-butoxide (24 g.) was stirred and heated in an atmosphere of nitrogen to 100° C. for 2 hrs. After cooling, the mixture was poured into 1000 ml. of 5% KOH solution and stirred overnight. The aqueous solution was extracted with ether (2×250 ml.) which was discarded. The aqueous solution was then acidified to pH 4.5 with conc. HCl. The product was filtered off, washed with water, dried in air and recrystallized from CHCl$_3$/isopropanol to yield the desired product, m.p. 229°–231° C.

According to this procedure, or an art-recognized modification thereof, any of the 3-hydroxypropyl side-chain materials used as starting materials in the reactions described in Examples 1–8 may be prepared.

PREPARATIVE EXAMPLE 4

1-(3,4-Dichlorophenyl)-4-hydroxy-3-(2-hydroxypropyl)-1,8-naphthyridin-2(1H)-one

A stirred mixture of gamma-valerolactone (40 g.), ethyl 2-(3,4-dichlorophenylamino)-nicotinate (20 g.) and potassium t-butoxide (30 g.) was warmed in an atmosphere of nitrogen to 110° C. and kept there for 5 hr. After cooling somewhat the product was poured into 1000 ml. of 5% KOH solution and was allowed to stir overnight. The basic solution was extracted with ether (2×500 ml.) and the aqueous solution was acidified to pH 5 with conc. HCl. The solid was filtered off, washed with water, dried in air then recrystallized from methanol/charcoal to yield the desired product, m.p. 232°–234° C.

This procedure or an art-recognized modification thereof may be used to prepare any of the 2-hydroxypropyl side-chain starting materials for use in Examples 1–8.

PREPARATIVE EXAMPLE 5

4-Hydroxy-3-(2-hydroxyhexyl)-1-phenyl-1,8-naphthyridin-2(1H)-one

A mixture of methyl 2-phenylaminonicotinate (5 g.), gamma-octanoic lactone (10 g.) and potassium t-butoxide (7.5 g.) was stirred in a nitrogen atmosphere and heated to 95° C. where it was held for 6 hrs. After cooling, the mixture was poured into 5% NaOH (200 ml.) and stirred overnight. Acidification to pH 4.6 yielded an oil, which was extracted with ether, washed with water, dried (Na$_2$SO$_4$), filtered, and evaporated to a small volume. Hexane was added until turbidity was noticed, and the mixture was allowed to stand for about 5 hrs. The solid was filtered off and recrystallized from CH$_2$Cl$_2$/isopropanol/isopropyl ether to produce the desired product, m.p. 184°–186° C.

This process, or an art-recognized modification thereof may be used to prepare any of the 2-hydroxyhexyl side-chain starting materials for use in Examples 1–8.

In general, by following the procedures described in Preparative Examples 1, 4, 5 or 6, or an art-recognized modification thereof, using lactones with desired substituents, other intermediates, II (B=O), useful for conversion to the products of the invention according to one of the methods described in Examples 1–8 and 10 may be prepared.

PREPARATIVE EXAMPLE 6

4-Hydroxy-3-(4-hydroxybutyl)-1-phenyl-1,8-naphthyridin-2(1H)-one

A mixture of methyl 2-phenylamino-nicotinate (100 g.), epsilon-caprolactone (1000 g.) and potassium t-butoxide (200 g.) was stirred at room temperature, in a nitrogen atmosphere, for ½ hr. It was heated at 45° C. for 1 hr. then at 85° C. for 2 hrs. and finally at 105° C. for 3 hr.

The hot mixture was poured carefully into 8 L of 5% KOH solution and was stirred overnight.

The mixture was extracted with 2 L of ether and the aqueous phase was retained. It was extracted again with a fresh 2 L of ether. The clear aqueous phase was adjusted to pH 4.5 with conc. HCl to yield a white solid which was filtered off, washed with water and dried to yield 4-hydroxy-3-(4-hydroxybutyl)-1-phenyl-1,8-naphthyridin-2(1H)-one, m.p. 205.5-206° C. (from isopropanol).

By substituting the relevant ester and lactone in this preparative example intermediates to many other compounds of the invention may be prepared.

PREPARATIVE EXAMPLE 7

4-Hydroxy-3-(4-methanesulfonyloxybutyl)-1-phenyl-1,8-naphthyridin-2(1H)-one

4-Hydroxy-3-(4-hydroxybutyl)-1-phenyl-1,8- naphthyridin-2(1H)-one (10 g.) was dissolved, with stirring, in Eaton's Reagent (10% $P_2O_5$ in methanesulfonic acid; 50 ml.) under a nitrogen atmosphere. The solution was heated to 55° C. where it was held for 3½ hr. It was then cooled and poured into a water/ice mixture. After stirring for several hours, the aqueous mixture was extracted (3x) with ethyl acetate (250 ml. each). The organic extract was separated, dried ($Na_2SO_4$), filtered and evaporated. The residue was stirred with a small volume of cold isopropanol and filtered to yield a brown solid, the mono-mesylate, which was used without further purification in Example 7.

PREPARATIVE EXAMPLE 8

2-(2-Chloro-3-nicotinoyl)-gamma-butyrolactone

A 1M solution of lithium bis(trimethylsilyl)amide (260 ml.; in hexane) was cooled to below −60° C. in a nitrogen atmosphere. To this was added a solution of gamma-butyrolactone (25.8 g.) in tetrahydrofuran (40 ml.) keeping the temperature below −60° C. The mixture was stirred for 1 hr., then to it was added a solution of ethyl 2-chloro-nicotinate (37.2 g.) in tetrahydrofuran (60 ml.) keeping the reaction temperature below −60° C. After stirring for 2 hrs., the reaction mixture was allowed to warm to room temperature and it was kept there overnight. Most of the solvent was removed then 500 g. of ice was added to the residue. The aqueous layer was adjusted to pH 5 and was then extracted with methylene chloride (3×500 ml.). The dried methylene chloride extract was evaporated to an oil which was purified by preparative high pressure liquid chromatography separation (Whatman Magnum 40 column; Partisil 40, ODS-3; $CH_3CN(25)$: $H_2O$ (75): $CH_3CO_2H(1)$) to yield the desired product, m.p. 50°-52° C.

PREPARATIVE EXAMPLE 9

4-Hydroxy-3-(2-hydroxyethyl)-1-(3-nitrophenyl)-1,8-naphthyridin-2(1H)-one

A mixture of 2-(2-chloro-3-nicotinoyl)-gammabutyrolactone (Preparative Example 8) (3 g.) and m-nitroaniline (3.67 g.) in methanol (50 ml.) was stirred in a nitrogen atmosphere and heated to an oil bath temperature of 130° C. The methanol was allowed to distil off. After 1½–2 hr., the mixture was allowed to cool. To the product was added 10% potassium hydroxide solution (200 ml.) and the mixture was stirred overnight. After adjusting the pH to 5.5, the solid product was filtered off, washed with water, dried, and recrystallized from isopropanol to yield the desired product, m.p. 244°-245° C. Conversion of this material to compounds of the invention may be accomplished by utilizing the procedures described in the Examples.

The following formulations exemplify some of the dosage forms in which the compounds of the invention may be employed. In each, the active ingredient is a compound represented by structural formula I, such as 9-(3-chlorophenyl)-3,9-dihydro-2-methyl-furo[2,3-b][1,8]naphthyridin-4(2H)-one, and is referred to as "active compound". However, any other compound falling within the scope of formula I could be substituted therefore.

FORMULATIONS

| FORMULATIONS Formulation I: Ointment | |
|---|---|
| Formula | mg/g |
| Active Compound | 1.0–20.0 |
| Benzyl Alcohol, NF | 10.0 |
| Mineral Oil, USP | 50.0 |
| White Petrolatum, USP to make | 1.0 g |

Procedure

Mix and heat to 65° C., a weighted quantity of white petrolatum, mineral oil, benzyl alcohol, and cool to 50°-55° C. with stirring. Disperse active compound in a portion of the mineral oil and then add to the above mixture with stirring. Cool to room temperature.

| Formulation II: Cream | |
|---|---|
| Formula | mg/g |
| Active Compound | 1.0–20.0 |
| Stearic Acid, USP | 60.0 |
| Glyceryl Monostearate | 100.0 |
| Propylene Glycol, USP | 50.0 |
| Polyethylene Sorbitan Monopalmitate | 50.0 |
| Sorbitol Solution, USP | 30.0 |
| Benzyl Alcohol, NF | 10.0 |
| Purified Water, USP to make | 1.0 g |

Procedure

Heat the stearic acid, glyceryl monostearate and polyethylene sorbitan monopalmitate to 70° C. In a separate vessel, dissolve sorbital solution, benzyl alcohol, water, and half quantity of propylene glycol and heat to 70° C. Add the aqueous phase to oil phase with high speed lightning stirring. Dissolve the active compound in remaining quantity of propylene glycol and add to the above emulsion when the temperature of emulsion is 37°–40° C. Mix uniformly with stirring and cool to room temperature.

| Formulation III: Gel | |
|---|---|
| Formula | mg./g |
| Active Compound | 1.0–20.0 |
| Propylene Glycol, USP | 300.0 |
| Butylated Hydroxytoluene | 5.0 |
| Carbomer 940 | 5.0 |
| Sodium Hydroxide (added as a 1% w/w solution in propylene glycol) | 0.7 |
| Polyethylene Glycol 400, USP | 669.3–688. |

Procedure

Prepare a 1% solution of the sodium hydroxide in propylene glycol and hold. Add approximately one-half the remaining propylene glycol, and the polyethylene glycol 400 to a suitable vessel and mix. Dissolve the butylated hydroxytoluene in this mixture. Disperse the carbomer 940 in the above mixture with vigorous agitation. Add the solution of sodium hydroxide with high speed agitation to bring pH up to 7 and recirculation until a thick gel forms. Dissolve the active compound in the remaining propylene glycol and add to the gel slowly as the gel is continuously recirculated.

| Formulation IV: Lotion | |
|---|---|
| Formula | mg/g |
| Active Compound | 1.0–20.0 |
| Carbomer 940 | 3.0 |
| Sodium hydroxide (charged as 4% w/w aqueous solution) | 0.05 |
| Isopropyl Alcohol | 40.00 |
| Purified Water, USP to make | 1.0 g |

Procedure

Prepare a 4% solution of sodium hydroxide in water. Heat the purified water to 60° C. Add carbomer 940 and mix at high speed until dispersed. Cool the above mixture to room temperature and slowly charge sodium hydroxide until uniform. Add 80% of isopropyl alcohol to the above with mixing. Dissolve the active compound in remaining isopropanol. Add this to the mixture with stirring. Adjust pH to 5.0 to 5.5 with sodium hydroxide, if necessary.

| Formulation V: Topical Aerosol | |
|---|---|
| Formula | mg/g |
| Active Compound | 1.0–20.0 |
| Caprylic/Capric Triglyceride | 50.00 |
| Mineral Oil | 20.00 |
| Specially Denatured Alcohol | 150.00 |
| Hydrocarbon Aerosol Propellant q.s. ad | 1.0 g |

Procedure

Add and mix the caprylic/capric triglyceride mineral oil and specially denatured alcohol in a suitable compounding tank. Add the active compound drug and continue mixing until the active compound is dissolved or dispersed uniformily. Fill the concentrate into cans and then fill the required amount of hydrocarbon aerosol propellant.

| Formulation VI: Tablets | | | |
|---|---|---|---|
| No. | Ingredient | mg/tablet | mg/tablet |
| 1. | Active Compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill needed. Dry the damp granules. Screen the dried the damp granules through a coarse screen (e.g., ¼") if granules if needed and mix with Item No. 4 and mix for 10–15 minutes. Add Items No. 5 and mix for 1–3 minutes. Compress the mixture to appropriate size and weight on a suitable tablet machine.

| Formulation VII: Capsules | | | |
|---|---|---|---|
| No. | Ingredient | mg/capsule | mg/capsule |
| 1. | Active compound | 100 | 500 |
| 2. | Lactose USP | 106 | 123 |
| 3. | Corn Starch, Food Grade | 40 | 70 |
| 4. | Magnesium Stearate NF | 4 | 7 |
| | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

| Formulation VIII: Parenteral | | |
|---|---|---|
| Ingredient | mg/vial | mg/vial |
| Active Compound Sterile Powder | 100 | 500 |

Add sterile water for injection or bacteriostatic water for injection, for reconstitution.

| Formulation VIX: Injectable | |
|---|---|
| Ingredient | mg/vial |
| Active Compound | 100 |
| Methyl p-hydroxybenzoate | 1.8 |
| Propyl p-hydroxybenzoate | 0.2 |
| Sodium Bisulfite | 3.2 |
| Disodium Edetate | 0.1 |
| Sodium Sulfate | 2.6 |
| Water for Injection q.s. ad | 1.0 ml |

Method of Manufacture

1. Dissolve parabens in a portion (85% of the final volume) of the water for injection at 65°–70° C.
2. Cool to 25–35° C. Charge and dissolve the sodium bisulfite, disodium edetate and sodium sulfate.
3. Charge and dissolve drug.
4. Bring the solution to final volume by added water for injection.
5. Filter the solution through 0.22 membrane and fill into appropriate containers.

6. Terminally sterilize the units by autoclaving.

The quantity of active compound in a unit dose of preparation may be varied or adjusted from 1 mg to 100 mg according to the particular application and the potency of the active ingredient. The compositions can, if desired, also contain other therapeutic agents.

The amount of active compound applied to the involved lesions may be varied depending upon the requirements of the patient, the severity of the condition being treated and the particular compound being employed. Determination of the proper dosage for a particular situation is within the skill of the art. For convenience, the total daily dosage may be divided and administered in portions during the day if desired.

I claim:

1. A method of treating hyperproliferative skin disease in a mammal comprising administering to said mammal in need of such treatment an anti-hyperproliferative skin disease effective amount of a compound represented by structural formula I or a salt or solvate thereof

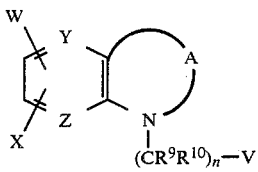

wherein:

A is

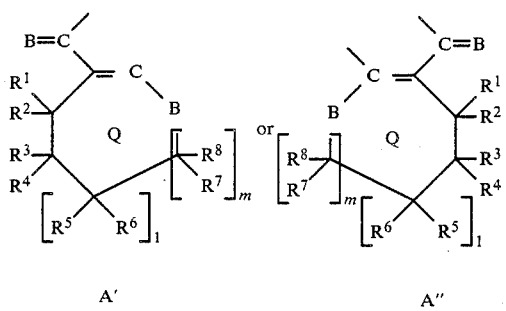

B is independently oxygen or sulfur;

$R^1$-$R^8$ may be the same or different and are hydrogen or alkyl having from 1 to 6 carbon atoms of two adjacent $R^1$-$R^8$ substituents may be combined to form an additional carbon to carbon bond;

l and m may be the same or different and are 0 or 1;

the ring labeled, Q, may optionally contain up to two additional double bonds;

n is 0, 1 or 2;

W and X may be the same or different and are hydrogen, hydroxy, alkyl having from 1 to 6 carbon atoms, halogen nitro, alkoxy having from 1 to 6 carbon atoms, trifluoromethyl, cyano, cycloalkyl having from 3 to 7 carbon atoms, alkenyloxy having from 3 to 6 carbon atoms, alkynyloxy having from 3 to 6 carbon atoms, $S(O)_p$-$R^a$ {wherein p is 0, 1 or 2 and $R^a$ is alkyl having from 1 to 6 carbon atoms}, $NHSO_2R^a$ (wherein $R^a$ is defined herein}, $NHSO_2CF_3$, $NHCOCF_3$, $SO_2NH_2$, $COR_b$ {wherein $R^b$ is OH, $NH_2$ or $OR^a$ (wherein $R^a$ is defined herein)}, O-D-$COR^b$ (wherein D is alkanediyl having from 1 to 4 carbon atoms and $R^b$ is defined herein}, or $NHCOR^c$ {(wherein $R^c$ is hydrogen, alkyl having from 1 to 6 carbon atoms, alkoxy having from 1 to 6 carbon atoms, $COR^d$ (wherein $R^d$ is hydroxy or alkoxy having from 1 to 6 carbon atoms) or $NHR^e$ (wherein $R^e$ is hydrogen or alkyl having from 1 to 6 carbon atoms)}, or phenoxy {wherein the benzene ring may be substituted with any of the other substituents W and X};

Y and Z may be the same or different and are CH or N;

V is phenyl, naphthyl, indenyl, indanyl, pyridyl, pyrimidinyl, thienyl, furyl or thiazolyl, any of which may be substituted with W and X as defined herein; and $R^9$ and $R^{10}$ are independently hydrogen or alkyl having from 1 to 6 carbon atoms.

2. The method of claim 1 wherein n is 0.

3. The method of claim 2 wherein Z is N.

4. The method of claim 3 wherein the compound has the structural formula:

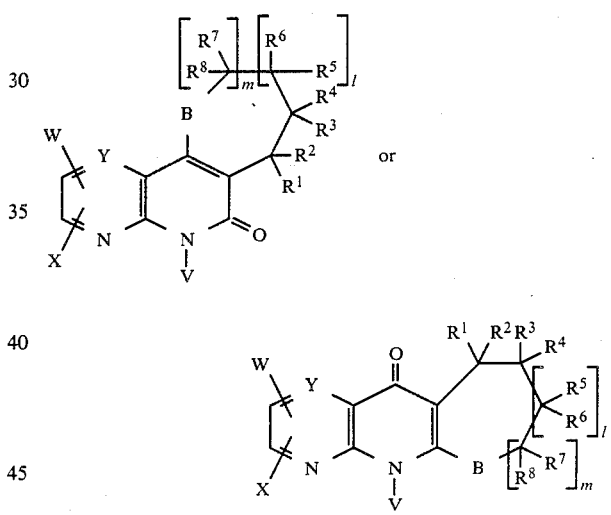

wherein B, W, X, Y, V, $R^1$ through $R^8$, l and m are as previously defined.

5. The method of claim 4 wherein Y is CH.

6. The method of claim 5 wherein l and m are 0.

7. The method of claim 5 wherein l and m are 1.

8. The method of claim 6 or 7 wherein B is oxygen.

9. The method of claim 6 or 7 wherein V is

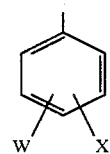

and W and X are as previously defined.

10. The method of claim 6 wherein the compound has the structural formula:

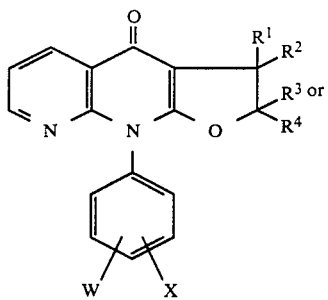

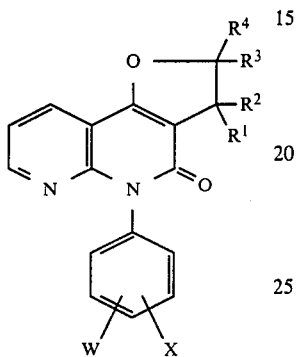

wherein W, X, R¹, R², R³ and R⁴ are as previously defined.

11. The method of claim 9 wherein the compound administered has the structural formula:

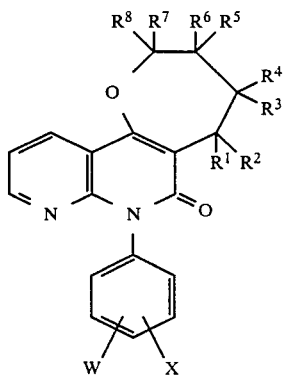

and wherein W, X, and R¹ through R⁸ are as previously defined.

12. The method of claim 10 wherein R¹ through R⁴ are hydrogen or methyl.

13. The method of claim 12 wherein zero or one of R¹-R⁴ is methyl and the rest are hydrogen.

14. The method of claim 13 wherein W is 3-chloro and X is hydrogen, chlorine or fluorine.

15. The method of claim 13 wherein W is 3-methoxy and X is hydrogen or fluorine.

16. The method of claim 13 wherein W and X are both hydrogen.

17. The method of claim 4 wherein the compound has the structural formula:

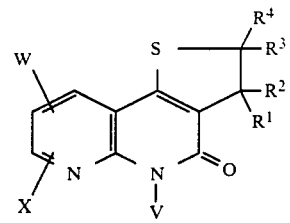

and W X, V and R¹ through R⁴ are as defined above.

18. The method of claim 17 wherein the compound administered has the structural formula:

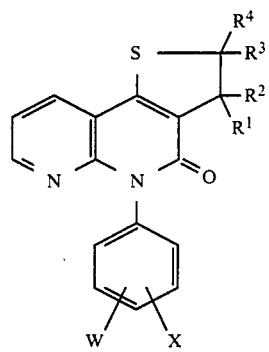

and W, X and R¹ through R⁴ are as previously defined.

19. The method of claim 18 wherein W is 3-chloro and X is hydrogen, chlorine or fluorine.

20. The method of claim 18 wherein W is 3-methoxy and X is hydrogen or fluorine.

21. The method of claim 18 wherein W and X are both hydrogen.

22. The method of claim 1 wherein the compound administered has the name:
3,5-dihydro-5-phenyl-furo[3,2-c][1,8]naphthyridin-4[2H]-one;
6-phenyl-2,3,4,6-tetrahydro-pyrano[3,2-c][1,8]-naphthyridin-5-one;
2-methyl-3,5-dihydro-5-phenyl-furo[3,2-c][1,8]-naphthyridin-4[2H]-one;
3,9-dihydro-9-phenyl-furo[2,3-b][1,8]naphthyridin-4[2H]-one;
3,9-dihydro-9-(p-methylphenyl)-furo[2,3-b][1,8]-naphthyridin-4[2H]-one;
3,9-dihydro-2-methyl-9-phenyl-furo[2,3-b][1,8]-naphthyridin-4[2H]-one;
3,5-dihydro-5-(p-methylphenyl)-furo[3,2-c][1,8]-naphthyridin-4[2H]-one;
3,5-dihydro-5-(p-fluorophenyl)-furo[3,2-c][1,8]-naphthyridin-4[2H]-one;
3,5-dihydro-5-(m-methoxyphenyl)-furo[3,2-c][1,8]-naphthyridin-4[2H]-one;
3,5-dihydro-5-(m-methylthiophenyl)-furo[3,2-c][1,8]-naphthyridin-4[2H]-one;
3,9-dihydro-9-(p-fluorophenyl)-furo[2,3-b][1,8]-naphthyridin-4[2H]-one;
3,9-dihydro-9-(m-methoxyphenyl)-furo[2,3-b][1,8]-naphthyridin-4[2H]-one;
3,9-dihydro-9-(m-methylthiophenyl)-furo[3,2-c][1,8]-naphthyridin-4[2H]-one;3,5-dihydro-5-(3,4-dichlorophenyl)-furo[3,2-c][1,8]-naphthyridin-4[2H]-one;
3,5-dihydro-5-(3,4-dichlorophenyl)-2-methyl-furo [3,2-c][1,8]-naphthyridin-4[2H]-one;

3,5-dihydro-5-(4-chlorophenyl)-furo[3,2-c][1,8]-naphthyridin-4[2H]-one;
3,5-dihydro-5-(3-chlorophenyl)-furo[3,2-c][1,8]-naphthyridin-4[2H]-one;
3,5-dihydro-5-(3-chlorophenyl)-2-methyl-furo[3,2-c][1,8]-naphthyridin-4[2H]-one;
3,5-dihydro-5-(4-fluorophenyl)-2-methy-furo[3,2-c][1,8]-naphthyridin-4[2H]-one;
3,5-dihydro-5-(3-methoxyphenyl)-2-methyl-furo [3,2-c][1,8]-naphthyridin-4[2H]-one;
3,5-dihydro-5-(3,5-dichlorophenyl)-furo[3,2-c][1,8]-naphthyridin-4[2H]-one;
3,5-dihydro-5-(3,5-dichlorophenyl)-2-methyl-furo [3,2-c][1,8]-naphthyridin-4[2H]-one;
3,5-dihydro-5-phenyl-2,2-dimethyl-furo[3,2-c][1,8]-naphthyridin-4[2H]-one;
3,5-dihydro-5-(3-methysulfonylaminophenyl)-2-methyl-furo[3,2-c][1,8]-naphthyridin-4[2H]-one;
3,5-dihydro-5-(3-methylsulfonylaminophenyl)-furo [3,2-c][1,8]-naphthyridin-4[2H]-one;
3,9-dihydro-9-(3,4-dichlorophenyl)-furo[2,3-b][1,8]-naphthyridin-4[2H]-one;
3,9-dihydro-9-(4-chlorophenyl)-furo[2,3-b][1,8]-naphthyridin-4[2H]-one;
3,9-dihydro-9-(3-chlorophenyl)-furo[2,3-b][1,8]-naphthyridin-4[2H]-one;
3,9-dihydro-9-(3-chlorophenyl)-2-methyl-furo[2,3-b][1,8]-naphthyridin-4[2H]-one;
3,9-dihydro-9-(4-fluorophenyl)-2-methyl-furo[2,3-b][1,8]-naphthyridin-4[2H]-one;
3,9-dihydro-9-(3-methoxyphenyl)-2-methyl-furo [2,3-b][1,8]-naphthyridin-4[2H]-one;
3,9-dihydro-9-(3,5-dichlorophenyl)-furo[2,3-b][1,8]-naphthyridin-4[2H]-one;
3,9-dihydro-9-(3,5-dichlorophenyl)-2-methyl-furo [2,3-b][1,8]-naphthyridin-4[2H]-one;
3,9-dihydro-9-(3-methylsulfonylaminophenyl)-2-methyl-furo[2,3-b][1,8]-naphthyridin-4[2H]-one;
6-(4-chlorophenyl)-2,3,4,6-tetrahydro-5H-pyrano[3,2-c]-[1,8]naphthyridin-5-one;
6-(3,4-dichlorophenyl)-2,3,4,6-tetrahydro-5H-pyrano [3,2-c][1,8]naphthyridin-5-one;
6-(4-methoxyphenyl)-2,3,4,6-tetrahydro-5H-pyrano [3,2-c][1,8]naphthyridin-5-one;
6-(4-methylphenyl)-2,3,4,6-tetrahydro-5H-pyrano [3,2-c][1,8]naphthyridin-5-one;
10-(3,4-dichlorophenyl)-2,3,4,10-tetrahydro-5H-pyrano-[2,3-b][1,8]naphthyridin-5-one;
10-(4-methoxyphenyl)-2,3,4,10-tetrahydro-5H-pyrano-[2,3-b][1,8]naphthyridin-5-one;
10-(4-chlorophenyl)-2,3,4,10-tetrahydro-5H-pyrano-(2,3-b][1,8]naphthyridin-5-one;
10-(4-methylphenyl)-2,3,4,10-tetrahydro-5H-pyrano-(2,3-b][1,8]naphthyridin-5-one;
10-phenyl-2,3,4,10-tetrahydro-5H-pyrano-[2,3-b][1,8]-naphthyridin-5-one;
7-phenyl-3,4,5,7-tetrahydro-oxepino[3,2-c][1,8]-naphthyridin-6[2H]-one;
7-(4-chlorophenyl)-3,4,5,7-tetrahydro-oxepino -[3,2-c][1,8]-naphthyridin-6[2H]-one;
7-(3-chlorophenyl)-3,4,5 7-tetrahydro-oxepino -[3,2-c][1,8]-naphthyridin-6[2H]-one;
7-(3-methoxyphenyl)-3,4,5,7-tetrahydro-oxepino -[3,2-c][1,8]-naphthyridin-6[2H]-one, or
7-(3-hydroxyphenyl)-3,4,5,7-tetrahydro-oxepino -[3,2-c][1,8]-naphthyridin-6[2H]-one.

23. The method of claim 1 wherein the compound is administered topically.

24. The method of claim 1 wherein the compound is administered orally.

25. The method of claim 1 wherein the compound administered is in the form of a pharmaceutical composition comprising the compound of formula I in combination with a pharmaceutically acceptable carrier.

26. The method of claim 25 wherein the pharmaceutical composition is in the form of a lotion.

27. The method of claim 25 wherein the pharmaceutical composition is in the form a cream.

28. The method of claim 25 wherein the pharmaceutical composition is in the form of an ointment.

29. The method of claim 25 wherein the pharmaceutical composition is in the form of an aerosol.

30. The method of claim 25 wherein the pharmaceutical composition is in the form of a gel.

* * * * *